(12) United States Patent
Schultheis et al.

(10) Patent No.: US 12,189,184 B2
(45) Date of Patent: Jan. 7, 2025

(54) ILLUMINATION SYSTEM HAVING LIGHT GUIDES WITH DIFFUSER ELEMENTS THAT EMIT RADIALLY

(71) Applicant: SCHOTT AG, Mainz (DE)

(72) Inventors: Bernd Schultheis, Schwabenheim (DE); Oliver Keiper, Hünstetten (DE); Jürgen Meinl, Hohenstein-Holzhausen (DE); Hubertus Russert, Jugenheim (DE); Jonas Grimm, Bad Schwalbach (DE); Lothar Willmes, Destrich-Winkel (DE); Martin Cramer, Wiesbaden (DE)

(73) Assignee: SCHOTT AG, Mainz (DE)

( * ) Notice: Subject to any disclaimer, the term of this patent is extended or adjusted under 35 U.S.C. 154(b) by 0 days.

(21) Appl. No.: 17/353,630

(22) Filed: Jun. 21, 2021

(65) Prior Publication Data

US 2021/0318494 A1 Oct. 14, 2021

Related U.S. Application Data

(63) Continuation of application No. PCT/EP2019/086345, filed on Dec. 19, 2019.

(30) Foreign Application Priority Data

Dec. 21, 2018 (DE) ...................... 10 2018 133 338.2

(51) Int. Cl.
*G02B 6/26* (2006.01)
*A61N 5/06* (2006.01)
(Continued)

(52) U.S. Cl.
CPC .............. *G02B 6/262* (2013.01); *A61N 5/06* (2013.01); *C03B 15/14* (2013.01); *C03C 3/091* (2013.01);
(Continued)

(58) Field of Classification Search
CPC ................ A61B 2018/2261; A61B 2018/2266
See application file for complete search history.

(56) References Cited

U.S. PATENT DOCUMENTS

| | | |
|---|---|---|
| 5,074,632 A | 12/1991 | Potter |
| 5,290,280 A | 3/1994 | Daikuzono |

(Continued)

FOREIGN PATENT DOCUMENTS

| | | |
|---|---|---|
| BR | 0107527 | 9/2003 |
| CN | 1953781 | 4/2007 |

(Continued)

OTHER PUBLICATIONS

Innovation Q+ NPL Search (Year: 2024).*
(Continued)

*Primary Examiner* — Anabel Ton
(74) *Attorney, Agent, or Firm* — Ruggiero McAllister & McMahon LLC

(57) ABSTRACT

An illumination system for medical therapeutic and/or diagnostic system is provided. The illumination system includes a laser light source and a light guide. The light guide has a proximal end that is connectable and/or assignable to the one laser light source. The light guide has a distal end with a diffuser element having a radial, spherical emission characteristic. The diffuser element includes a diffuser main body made of an inorganic material, in particular a glass, a glass ceramic, a glass-like substance or a composite substance of the aforementioned substances. The diffuser main body has a scattering element and has a surface that is pore-free and smooth.

32 Claims, 6 Drawing Sheets

(51) Int. Cl.
*A61N 5/067* (2006.01)
*C03B 15/14* (2006.01)
*C03C 3/091* (2006.01)
*F21V 8/00* (2006.01)

(52) U.S. Cl.
CPC ......... *G02B 6/0006* (2013.01); *G02B 6/0051* (2013.01); *A61N 2005/063* (2013.01); *A61N 5/067* (2021.08)

(56) References Cited

U.S. PATENT DOCUMENTS

| | | |
|---|---|---|
| 6,366,719 B1 | 4/2002 | Heath |
| 6,810,184 B2 | 10/2004 | Skutnik |
| 11,255,491 B2 * | 2/2022 | Dutta ..................... F21K 9/232 |
| 2004/0036975 A1 | 2/2004 | Slatkine |
| 2005/0105877 A1 * | 5/2005 | Nappi ..................... G02B 6/262 385/139 |
| 2006/0018596 A1 * | 1/2006 | Loebel .................. G02B 6/262 385/38 |
| 2007/0225695 A1 | 9/2007 | Mayer |
| 2007/0297190 A1 * | 12/2007 | Ng ....................... A61N 5/0601 362/558 |
| 2008/0161748 A1 | 7/2008 | Tolkoff |
| 2009/0204111 A1 | 8/2009 | Bissig |
| 2009/0318912 A1 | 12/2009 | Mayer |
| 2010/0298738 A1 | 11/2010 | Felts |
| 2013/0314940 A1 | 11/2013 | Russert |
| 2014/0268815 A1 | 9/2014 | Li |
| 2014/0270639 A1 | 9/2014 | James, III |
| 2016/0130175 A1 | 5/2016 | Siebers |
| 2017/0176660 A1 * | 6/2017 | Mirsepassi ............. A61B 90/36 |
| 2017/0367569 A1 | 12/2017 | Ohara |
| 2018/0299614 A1 | 10/2018 | Schwagmeier |
| 2020/0222712 A1 | 7/2020 | Schultheis |

FOREIGN PATENT DOCUMENTS

| | | |
|---|---|---|
| DE | 10129029 | 12/2002 |
| DE | 112014001293 | 11/2015 |
| DE | 102014222645 | 5/2016 |
| DE | 102015119875 | 12/2016 |
| DE | 112015006369 | 12/2017 |
| EP | 0792663 | 11/2001 |
| EP | 3140688 B1 * | 2/2015 |
| EP | 3184885 | 6/2017 |
| EP | 3185057 | 6/2017 |
| JP | H0394744 | 4/1991 |
| JP | 2000081516 | 3/2000 |
| JP | 2011248022 | 12/2011 |
| JP | 2018130530 | 8/2018 |
| WO | 2008024397 | 2/2008 |
| WO | 2017103796 | 6/2017 |
| WO | 2019063799 | 4/2019 |

OTHER PUBLICATIONS

English translation of International Preliminary Report on Patentability dated Jun. 24, 2021 for PCT/EP2019/086345, 12 pages.
English translation of International Search Report dated Jun. 10, 2020 for PCT/EP2019/086345, 4 pages.

* cited by examiner

ILLUMINATION SYSTEM HAVING LIGHT GUIDES WITH DIFFUSER ELEMENTS THAT EMIT RADIALLY

CROSS REFERENCE TO RELATED APPLICATIONS

This application is a continuation of International Application PCT/2019/086345 filed Dec. 19, 2019, which claims the benefit of German Application 10 2018 133 338.2 filed Dec. 21, 2018, the entire contents of all of which are incorporated herein by reference

BACKGROUND

1. Field of the Invention

The invention relates to an illumination system, in particular for medical therapeutic and/or diagnostic system, comprising at least one laser light source and a light guide which, at a proximal end, is connectable and/or assignable to the at least one laser light source, and which comprises at the distal end of the light guide a diffuser element. The invention further relates to a method for producing the illumination system.

2. Description of Related Art

Such illumination systems find increasing use in medicine. In this case, it is possible to classify the following focuses of application: photodynamic therapy (PDT) and/or photoimmunotherapy (PIT) for tumor therapy, endovenous laser treatment (EVLT) for treating varicose veins, laser interstitial thermal therapy (LITT) and other applications, inter alia in the fields of dentistry, ophthalmology or dermatology.

Photodynamic therapy (PDT) is a minimally invasive option for therapy in the case of various cancers. PVD is understood to be a method for treatment of tumors and other tissue changes (such as neovascularization) using light in combination with a light activatable substance. At the start of the treatment, light-sensitive substances, so-called photosensitizers, are injected into the patient's bloodstream intravenously, said substances accumulating in or on the cancerous cells. These natural photo substances accumulate in the tumor cells and cause a pronounced light sensitivity there. To this end, a plurality of cannulas (typically up to 8) can be pierced into the tumor tissue and a light guide with a diffuser element is introduced into each cannula, the diffuser elements having to be disposed in spatially distributed fashion over the tumor tissue. Laser light, as a rule with wavelengths in the visible spectral range, for example green light with a wavelength of 532 nm or red light with a wavelength of 690 nm, is coupled into the diffuser elements by the light guides such that the tumor tissue is illuminated as uniformly as possible from the inside. In the process, aggressive oxygen radicals form in these cells and selectively destroy the tumor cells. In contrast to the diseased cells, the healthy cells remain untouched by this chemical reaction. The precise mode of action is described, inter alia, in "Photodynamic Therapy of Cancer", Cancer Medicine 2003.

In photoimmunotherapy (PIT), the photosensitizer is bound to an antibody so that the medicament can be released more selectively to the tumor tissue. The antibody is specific against a protein present on the surface of the tumor, and so it specifically approaches the tumor. Then, the tumor is irradiated with light, triggering the destruction thereof. Ideally, the photosensitizer bound to the antibody reaches the most sensitive part of the tumor cell, such as the lysosomes, which contain a digestion enzyme. The destruction of the lysosome causes the cancerous cells to digest themselves on account of the release of the enzymes. This leads to a more selective and focused treatment effect and also allows the use of lower doses of photosensitizers and also lower doses of light.

Here, a distinction is made between cylindrical diffusers with typical active lengths of 10 to 50 mm, spot diffusers which generate a forwardly directed illumination cone, and point emitters which have a radial light emission.

What it comes down to in the operating state of cylindrical diffusers is that, in particular, a lateral emission of the diffuser elements should be as homogeneous as possible over their length. This applies both axially, i.e., the emission intensity is the same within the scope of the homogeneity requirements at all points along any line from the proximal to the distal end in the direction of the longitudinal axis, and radially, i.e., the emission intensity is also same within the scope of the homogeneity requirements at all points on any circumferential line along the longitudinal axis, as a result of which these diffusers almost act as Lambertian emitters. At the same time, high scattering efficiency should also be obtained in many applications in order to ensure as little heat input into the tissue as possible. However, there are applications where a certain amount of heat input may be required.

What it comes to down to in the case of diffusers embodied as point emitters is that, in particular, there is a uniform light distribution over the whole spherical space.

Known examples include diffuser elements made of a thin silicone cylinder, in which scattering particles in the form of titanium oxide nanoparticles are embedded. The document DE 10 129 029 A1 describes a flexible apparatus for thermally atrophying biological tissue by means of laser radiation, comprising a light guide carrying the laser radiation, the distal end of said light guide being surrounded by an enveloping tubing that is transparent to the laser radiation, that projects beyond the fiber end and that is filled with a silicone matrix in the volume thereof located in front of the fiber end, with scattering particles being embedded in said silicone matrix, wherein non-scattering particles with diameters of a few nanometers and preferably made of silicon dioxide are mixed with a concentration range of preferably 1-10% into a plastics matrix, preferably made of silicone, and the distal end of the enveloping tubing is tightly sealed by an end piece that is transparent or opaque to the laser radiation.

However, it is very complicated and costly to produce these with a sufficient emission homogeneity. Conglomerations of the scattered particles often yield emission spots whose intensity then is significantly above average. Moreover, it is only possible to apply low laser powers.

As a rule, these light guides with the diffuser elements are used only once and are disposed of after each treatment. Therefore, there are also certain pressures on the costs in relation to the production costs. Therefore, there also intense deliberations in respect of reusable solutions. Such solutions must then be preparable in accordance with the relevant known standards, for example disinfectable and/or sterilizable. In this case, cleaning/disinfection methods with strongly alkaline solutions and sterilization by means of autoclaving at temperatures up to 135° C. and typical steam pressures of approximately 3 bar should be mentioned, in particular, as preparation methods. Typically, a few ten to several hundred of such preparation cycles are assumed. This places great demands on the thermal, chemical and hydrolytic durability. Therefore, light guide and diffuser approaches made of glass or quartz glass fibers are then particularly suitable.

In the case of EVLT, the treating physician introduces a catheter into the affected vein via a tiny puncture site, said catheter serving as a guide for the vein laser. As a result of the targeted lateral emission of the laser power by means of the diffuser, the vessel inner wall is subsequently strongly heated, leading to the vein collapsing and becoming sealed. The pathological return flow of the venous blood is consequently prevented. As a consequence, the vein hardens, regresses and is able to be broken down by the body. As a rule, so-called ring or double ring fire systems are currently used as emission elements in this case. The laser light is emitted radially in the form of a relatively sharply delimited ring or double ring light to the tissue surrounding the vein. Here, for uniform treatment, the light guide with the emission element is often manually pulled through the vein section to be treated at a rate that is as constant as possible; this complicates the application, since further cell damage may arise at a point in the case of non-compliance or excessive dwell time.

A cylindrical diffuser of the kind used in PDT applications would bring advantages here. However, EVLT treatment requires significantly higher laser powers. By way of example, laser power is typically between 10 and 50 W at wavelengths in the NIR range, i.e., between approximately 800 nm and 1,480 nm, which is currently provided using diode lasers (for example, 810 nm, 940 nm or 1480 nm) or Nd:YAG lasers (1064 nm) In the meantime, longer wavelengths around 2 m have also become established for EVLT treatment. In this case, Tm:YAG lasers (1.9 µm) and Ho:YAG lasers (2.1 µm) are used, for example. On account of the absorption properties of tissue, lower laser powers, typically <10 W, are required at these wavelengths. However, the use of light guides made of fused silica is already mandatory here, in particular for supplying the laser light.

LITT is a minimally invasive method that is used for local tumor destruction. The tumor is punctured under visualization (e.g., sonography/MRI), one (or more) laser fiber(s) are introduced into the focus of the tumor, and sclerosis is induced in the latter by thermal energy. Use is made here, in particular, of Nd:YAG lasers (1064 nm) and diffuser tip applicators. The laser power is approximately 5 to 8 W (see, inter alia, in "Laserinduzierte Interstitielle Thermotherapie (LITT) bei malignen Tumoren" BÄK and KBV January 2002).

Further diffuser approaches are known from the documents set forth below, it being possible to classify these diffuser approaches in four categories: volume-scattering diffusers, fibers with applied scattering particles, diffusers produced by means of laser processing and diffusers formed from laterally emitting fibers.

Byway of example, volume-scattering diffusers are described in the document EP 3 184 885 A1. The latter describes a diffuser at the end of an optical fiber made of quartz glass, the application of a scattering compound to the distal fiber and end securing said scattering compound to the diffuser being provided for producing the diffuser. The application of the scattering compound comprises the steps of (a) providing a $SiO_2$ grain containing amorphous $SiO_2$ particles and consisting to at least 90% by weight of $SiO_2$, (b) providing a hollow body made of glass with a void wall surrounding a void that is open to the outside, (c) forming a bed of the $SiO_2$ grain in the void and introducing the fiber end into the void such that at least a part of the fiber end protrudes into the bed, (d) thermally compressing the bed to form a porous sintering compound consisting to at least 90% by weight of $SiO_2$, said sintering compound being at least partly surrounded by a glass jacket. A disadvantage of such approaches is that these volume-scattering approaches are accompanied by a strong exponential drop in the intensity. Additionally, porous materials are not preferred in view of the preparability thereof in medical applications. Moreover, bodily fluids can penetrate the scattering, porous material during the treatment such that there is a significant alteration or even elimination of the scattering effect.

U.S. Pat. No. 6,810,184 B2 describes an approach in which nanoporous silicon dioxide-clad optical fibers are used to make fibers having integrally formed diffusion tips and diffusion tips that can be fused to other fibers. The disclosed diffusers can be fabricated to be cylindrical with light diffusing along its length, spherical with light radiating outwardly in a spherical pattern, or custom shaped to illuminate irregular surfaces or volumes. Gradient and step index properties can also be achieved.

Documents EP 2 062 077 A4, US 2009/0204111 A1 and DE 10 2015 119 875 A1 describe diffusers in which, for the production thereof, structures are introduced in or applied to the fiber by means of a laser.

Document EP 2 062 077 A4 or WO 2008/024397 A2 describes, inter alia, a diffuser for outputting optical energy with a high power density to a treatment site at the distal end of at least one optical fiber, wherein the diffuser is a section with a predetermined length of the distal end of at least one optical fiber, and scattering centers which are positioned in the section of predetermined length at the distal end of the optical fiber, the scattering centers causing some of the input optical energy to emerge radially on the treatment site. Here, provision is made for the scattering centers to be arranged in the predetermined length of the fiber core or in, or in the vicinity of, an interface between the fiber core and the cladding in the predetermined length. The scattering centers are defects of the fiber core, for example nano cracks or nano voids, which reduce localized refractive index differentials either in the core or in, or in the vicinity of, the interface between the core and the cladding. The scattering centers can be scattering particles contained in the core or in the cladding of the core. In addition of the complicated and hard to control introduction in respect of, e.g., the distribution and/or the size of the aforementioned nano cracks or nano voids, the latter may also have a negative effect on the susceptibility of the component to fracture. Moreover, none of the aforementioned approaches should be expected to obtain the required homogeneity, either on account of the exponential drop of the lateral emission in the case of a sufficiently homogeneous configuration of the scattering centers or on account of non-uniform distributions.

Document US 2009/0204111 A1 describes a laser delivery system comprising an optical fiber with (i) a core and a cladding layer covering at least part of the core, wherein the cladding layer has a lower refractive index than the core and (ii) a non-feature portion and a feature portion having features that force the light to couple out radially from the feature portion and provide a desired radial light output pattern. Here, provision is made for the features to be selected from a group consisting of spiral structures, radial cuts, axial cuts and a combination thereof.

Document DE 10 2015 119 875 A1 describes an optical waveguide comprising a light wave-guiding core and a region in the optical waveguide, wherein micro-modifications are arranged in the region of the optical waveguide and wherein the arrangement of the micro-modifications is ordered. The method for introducing the micro-modifications into optical waveguides comprises the steps of (a) securing an optical waveguide in a holder, wherein the optical waveguide and/or the holder are movably mounted, (b) focusing high-energy radiation at a focal position, wherein the focal position is positionable in the interior of the optical waveguide, wherein the radiation is produced by radiation source in pulse operation and wherein the focusing device for focusing the high-energy radiation is movably mounted, and (c) moving the focal position through the optical waveguide, wherein the movement of the focal position in the interior of the optical waveguide is chosen on the basis of the repetition rate.

Document WO 2017/103796 A1 describes a further illumination system for emitting light. Here, the illumination system and describes a light guide connected to a light-scattering element.

A further document of the applicant, PCT/EP2018/076487, describes an illumination system, particularly for a medical therapeutic and/or diagnostic system, comprising at least one laser light source, and a light guide that, on its proximal end, can be connected to and/or associated with the at least one laser light source, and, on its distal end, comprises a cylindrical diffuser element with a longitudinal axis extending perpendicularly to the input coupling face of the light guide into or in the diffuser element, said diffuser element emitting light over the active length thereof laterally to the longitudinal axis, during the operating state thereof. The diffuser element comprises at least one diffuser main body containing at least one scattering element, said at least one scattering element preferably being oriented along the longitudinal axis of the diffuser main body. By way of such an arrangement, it is possible to achieve a homogeneous intensity distribution of the lateral emission along the length of the diffuser in the operational state. However, this also requires a relatively large extent of the diffuser main body in the longitudinal direction.

SUMMARY

Therefore, the object of the invention is that of providing a diffuser, in particular for an illumination system, in particular for medical therapeutic and/or diagnostic system, said diffuser being even more compact than an elongate diffuser and, in particular as virtually a point emitter, emitting in homogeneous fashion, ideally in spherical fashion, into space or into the surrounding tissue.

It would therefore be advantageous to provide a compact diffuser element, in which the disadvantages of the approaches described at the outset, such as porosity and low laser resilience, are significantly reduced. In this context, it would be advantageous if this diffuser element were able here to emit uniformly with a high efficiency. It is furthermore an object of the invention to provide a suitable method for the cost-effective production thereof.

According to a first aspect, the subject matter of the invention relates to an illumination system, in particular for medical therapeutic and/or diagnostic system, comprising at least one laser light source and a light guide which, at a proximal end, is connectable and/or assignable to the at least one laser light source, and which comprises at the distal end of the light guide a diffuser element which has a substantially radial, spherical emission characteristic, wherein the diffuser element comprises at least one diffuser main body and the diffuser main body comprises an inorganic material, in particular a glass, a glass ceramic, a glass-like substance or a composite substance of the aforementioned substances, and preferably at least one scattering element), and wherein the surface of the at least one diffuser main body is pore-free and smooth.

The term "pore-free and smooth" is understood to mean a very high surface quality of the diffuser main body, corresponding to a fire-polished surface quality. This fire-polished surface quality of the diffuser main body can be produced by the material and the processing of the diffuser main body itself, for example if a glass or glass ceramic is chosen as the material. However, a fire-polished or equivalent surface quality, at least in respect of the pore-free parameter of the diffuser main body, can also be brought about by a jacket, wherein the at least one diffuser main body advantageously comprises a jacket at least in part or in sections, said jacket surrounding the diffuser main body at least in part or in sections or else in full and said jacket forming the pore-free and smooth surface.

A pore-free and smooth surface of the diffuser is consequently also substantially sealed, leading to the advantage of a reduced reaction with liquids or of acting liquids having less of an influence on the emission behavior.

An element able to bring about scattering, preferably during operation, is referred to as a scattering element below. This includes a scattering region which can comprise a volume region and brings about the scattering. The scattering itself is brought about by at least one scattering center in the scattering region. Byway of example, a scattering center can comprise a particle or a pore. Here, provision is made, inter alia, for a density and the size distribution of these scattering centers to be set in defined fashion, and consequently for the scattering effect to be influenced in targeted fashion, during the production of the illumination system according to the invention.

The illumination system can comprise a laser light source which emits light, i.e., electromagnetic radiation, within a certain spectral range in the operational state. In a particularly preferred embodiment of the invention for medical therapy, for instance for so-called photodynamic therapy (PDT applications), use is preferably made of lasers that emit at a wavelength matched to the previously administered biochemically modified dye (photosensitizer), usually in the visible range, for example in the green spectral range at 532 nm or in the red spectral range at 690 nm, for example.

The light guide is preferably connected at its proximal end to the laser light source using a connector. Here, the proximal end refers to the end of the light guide where light is coupled in. At the distal end, the light guide comprises the diffuser element. In this context, light guide and diffuser element are embodied in such a way in a particularly preferred embodiment that they can be introduced directly, or by means of a cannula, into a tumor tissue that has formed within healthy tissue. Here, the distal end refers to the other end of the light guide which, as a rule, is arranged at a distance from the proximal end of the light guide and from which light, in particular, emerges.

In this case, the laser radiation can reach into the diffuser element by way of light input coupling at the diffuser element and said laser radiation is scattered multiple times in the diffuser element and emitted via the surface thereof, substantially in radial spherical fashion.

Within the meaning of the present invention, a radial, spherical emission characteristic of the diffuser element means a spherical emission which is uniform in the ideal case. A perfect spherical emission characteristic in this sense accordingly corresponds to an emission which, proceeding from a point, has an angle-independent uniform form and has the same intensity independent of angle, in a manner comparable to a Lambertian emitter.

In this case, a certain angle dependence of the emission may be given or even desirable for certain applications, meaning that the emission can be stronger or weaker under certain angles, i.e., there is a different emission intensity in relation to the angle. The angle dependence of the emission can also be used in targeted fashion to compensate an inhomogeneity in the emission, for instance as a consequence of different concentrations of the scattering centers or on account of different path length through the diffuser main body.

However, it preferably comes down to an emission that is as homogeneous as possible into a sphere surrounding the diffuser element. In particular, intensity peaks should be avoided. As a result of the photo-induced biochemical reaction, as described at the outset, there can ideally be necrosis of the tumor tissue following the treatment within the scope of photodynamic therapy.

As a rule, quartz fibers can be used as light guides, wherein the connectors can be embodied, as a rule, as coaxial plug-in connectors, so-called SMA connectors or else FC connectors, in which the fibers are adhesively bonded into the connector. Connectors with nickel silver sleeves can also be advantageous in respect of the thermal resilience; here, the light guide is introduced or crimped into the nickel silver sleeve in interlocking fashion byway of a plastic deformation.

Moreover, in the case of greater laser powers, use can also be made of connectors in which the fiber end of the light guide is protected by conical prism; this may be advantageous in the case of misalignments.

In most embodiments the light guide can be equipped with quartz glass with a core having a refractive index $n_1$ and the core diameter DC of usually between 50 and 1000 μm, preferably between 200 and 600 nm, and comprise cladding with the refractive index $n_2$, wherein $n_1 > n_2$ applies. Usually, such a fiber also has an outer polymer layer referred to as a buffer, consisting of polyamide or polyimide, for example. The numerical aperture NA usually obtainable there with is approximately 0.22. Quartz glass-based light guides are also known and these can have a numerical aperture NA of up to 0.4 using certain dopants. Light input coupling is implemented by way of an input coupling face, which is formed by a connecting zone of the diffuser main body.

To obtain the desired emission characteristic, the diffuser main body preferably has certain geometric dimensions and relationships, which will be discussed in more detail below.

To this end, the diffuser main body preferably has a substantially spherical, elliptical, drop-shaped or cylindrical geometry in order to meet the demand of a substantially radial, spherical emission characteristic. At the same time, such spherical, elliptical or drop-shaped geometries also very advantageously facilitate a very compact structure of the diffuser main body. Here, the invention also comprises combinations of these basic shapes, i.e., diffuser main bodies that have a geometry that is pieced together from these basic shapes.

Further basic shapes also comprise, for example, a short cylinder section or, e.g., drop-shaped or oval geometries, or else dome-shaped geometries. The inventors have discovered that the desired emission characteristic can also be obtained with a cylindrical or elongate geometry of the diffuser main body if very specific boundary conditions for such structures are observed depending on the material and scattering centers, which will be discussed more in depth below.

Further, the diffuser main body comprising a region of the surface that deviates from these basic shapes in terms of its geometry is not precluded here. This is due to the circumstances of the diffuser main body being connected to the light guide and this being able to be realized most easily byway of a correspondingly flattened region of the surface of the diffuser main body. Accordingly, this flattened region can have a flat or planar embodiment, with however the assumption being made that the remaining surface of the diffuser main body has a geometry deviating therefrom and, in particular, does not have a planar or flat embodiment.

Furthermore, the radial, spherical emission characteristic is promoted by an extent of the diffuser main body in which the greatest extent LD of the diffuser main body in a first direction is no more than 10 times, preferably 5 times and particularly preferably 2.5 times the extent of the diffuser main body in a second direction DD perpendicular to this first direction, furthermore preferably no more than 2 times and again particular preferably no more than at 1.5 times. In this case, the extent in the direction DD refers to an extent in the direction perpendicular to the light input coupling, i.e., perpendicular to the longitudinal direction of the light guide in the region of the input coupling. The extent in the direction LD refers to the length of the diffuser main body along its longitudinal axis provided the latter has a rather oval or elliptical manifestation, i.e., parallel to the direction of the light input coupling or in a direction parallel to the longitudinal direction of the light guide in the region of the input coupling.

The following applying was found to be advantageous as a matter of principle: LD≥DD.

In a particularly preferred embodiment, the extent of the diffuser main body in a first direction equals the extent of the diffuser main body in a second direction perpendicular to this first direction, as a result of which a spherical embodiment is provided.

The maximum extent of the diffuser main body LD in one direction can be in the range between 200 μm and 10 mm or even greater. An expedient length and/or width of the diffuser main body depends on a plurality of factors in this case. Thus, the type of scattering centers and the concentration thereof in the volume of the diffuser main body influences the scattering length LS, which denotes the distance from the light input coupling point where the light intensity has dropped to the value of 1/e or 36.8%. Expediently, the maximum extent LD of the diffuser main body is determined thereby, wherein it was found to be advantageous for a homogeneous emission characteristic if the maximum length LD is no more than three times the scattering length, and so the following applies: LD≤3*LS, preferably LD≤2.5*LS and particularly preferably LD≤2 LS. LD=LS in a particularly preferred embodiment.

Then, should the scattering length be 10 mm, the diffuser main body can advantageously likewise be 10 mm long.

In general, expedient embodiments lie between 250 μm and 4 mm, and preferably between 300 μm and 3 mm.

Advantageously, the width of the diffuser main body is determined by the core diameter of the light guide. The light guide can comprise a single fiber, for example a monomode or multimode optical fiber comprising a core with a core diameter and cladding, or a fiber bundle with the fiber bundle diameter. For the quartz fibers used, the external diameters of the light guide usually lie between 200 μm and 800 μm.

In a preferred embodiment, the light guide can comprise a single fiber with a core with a core diameter and a cladding, wherein the diameter of the diffuser main body in the region of the input coupling face is greater than or at least equal in size to the core diameter of the light guide in the region of the input coupling face. Likewise preferably, the ratio of core diameter of the light guide to diameter or width of the diffuser body is ≤1.0 to 0.7 in this case, and particularly preferably ≤1.0 to 0.8.

In a further preferred embodiment, the light guide can comprise a fiber bundle with a fiber bundle diameter, wherein the diameter of the diffuser main body in the region of the input coupling face is greater than or equal in size to the fiber bundle diameter of the light guide in the region of the input coupling face. Likewise preferably, the ratio of fiber bundle diameter of the light guide to diameter or width of the diffuser body is ≤1.0 to 0.7 in this case, and particularly preferably ≤1.0 to 0.8.

In a further embodiment, the light guide can be embodied as a rigid fiber rod. Here, provision can be made for the diffuser main body to be adhesively bonded or spliced to the distal end of the rigid optical fiber rod. To this end, provision can be made for the optical fiber rod to be tapered to a cone at the distal end, in such a way that the diameter of the distal end face is virtually the same size as the diameter of the diffuser main body. Furthermore, provision can be made for the rigid fiber rod to have at least one bend. In this way, it is particularly easily possible to use the illumination system according to the invention with a rigid fiber rod and a diffuser element in the field of dentistry, for example for treating mucositis. In this context, it is advantageous that it is possible to provide a system that is compatible to so-called curing rods that are used in the field of dentistry. Such curing rods, as a known from DE 10 2013 208 838 A1, for example, as a rule consist of fiber rods that may have a bent and tapered embodiment; using such curing rods, it may be possible, for example, to cure dental fillings using blue light.

For most applications of the illumination according to the invention, it is expedient if the dimensions of the diffuser main body are selected in such a way that the illumination system facilitates an emission with a small percentage deviation from a mean emission intensity during the operational state. Here, it is particularly expedient for most envisaged applications if the intensity distribution of the emission deviates by no more than ±30% and preferably by no more than ±20% from a sliding mean value in order to obtain an optimal treatment success. A smaller deviation, for instance no more than 15% or even no more than 10%, is even better for most applications. Applications where a certain deviation in the emission characteristic is desirable are excluded herefrom.

To determine the emission characteristic, it is possible to measure the intensity, luminance, relative luminance or brightness at a plurality of points, for instance along a straight line on the surface of the diffuser main body. The mean emission intensity can then be based on the mean value of all values measured along the straight line.

The statement that in the operational state the illumination system has an intensity distribution of the emission which deviates by no more than ±30% and preferably by no more than ±20% from a sliding mean value bases this deviation on a sliding mean, with the averaging being understood to be over a plurality of points lying next to one another on the straight line.

Devices and/or measured for homogenizing the lateral emission, i.e., in a direction perpendicular to the longitudinal direction of the light guide, are provided at the transition region between the light guide and diffuser main body. Byway of example, these include layers at the distal end of the light guide for preventing a forwardly directed emission from the distal end or for reflecting the latter back and hence providing these to the scattering processes in the diffuser main body again and, secondly, for avoiding scattered light effects and/or light reflections at the diffuser main body.

This allows the provision of diffuser elements that emit homogeneously in the operational state for medical therapies as mentioned at the outset in a reproducible and also cost-optimized manner.

The homogenization of the intensity of the mission can be assisted if the diameter the diffuser main body, in which the scattering elements are embedded, is equal to or greater than a core diameter or fiber bundle diameter of the light guide. In this case, the diameter of the diffuser main body relates to the extent of the diffuser main body in a direction perpendicular to the longitudinal direction of the light guide, and consequently corresponds to the aforementioned value DD.

A ratio of core diameter or fiber bundle diameter of the light guide to the diameter of the diffuser main body of ≤1.0 to 0.3, particularly preferably of ≤1.0 to 0.5, was found to be particularly expedient.

Here, a core diameter or fiber bundle diameter only slightly smaller than the diameter can reduce an intensity peak at the input coupling point, i.e., the transition region of the light guide and diffuser main body.

By contrast, a core diameter or fiber bundle diameter significantly smaller than the diameter of the diffuser main body, i.e., a ratio of <0.8, can lead to an intensity reduction at the input coupling point, which may likewise be advantageous for certain requirements.

Moreover, if the ratio is between 1 and 0.9, it was found that a particularly robust mechanical coupling or connection can be obtained between the light guide and diffuser main body, for example by splicing.

On the other hand, exemplary embodiments in which, for example, a diffuser main body embodied virtually as a ball with a 1 mm diameter is connected to a fiber with a core diameter of 400 µm, in particular by splicing, are also conceivable. In this case, the ratio can also be significantly smaller than 1; the ratio is 0.4 in this example.

In a preferred embodiment, the diffuser element has a connecting zone between the diffuser main body and the distal end of the light guide, said connecting zone being produced in interlocking and/or integral fashion by means of adhesive bonding, splicing or crimping and connecting the diffuser main body and the core diameter or the fiber bundle diameter of the light guide. In this context, the term splicing means a secure, integral connection of diffuser main body and light guide by partial melting, i.e., a softening by the application of heat, of at least one of the two bodies to be connected, preferably the light guide, and subsequent bringing into contact. Then, a secure connection can set in during cooling.

To this end, use can be made of a refractive index-matched, highly transparent adhesive. During splicing, the light guide and the diffuser main body are partially melted or melted by means of a corona discharge and/or by means of the laser, usually a $CO_2$ laser, and are brought together. Depending on the material used for the diffuser main body and the light guide, it may be necessary to use an intermediate medium for the purposes of matching the coefficients of the thermal expansion. In the case of glass/quartz fusion, this may be the soldering or transition glass or an optical adhesive or cement.

To match possibly different coefficients of thermal expansion, it may be advantageous if an intermediate medium is additionally provided in the connecting zone between the diffuser main body and the distal end of the light guide. By way of example, this could be a transition glass or soldering glass. On the other hand, this can also be a transparent, permanently elastic adhesive. Moreover, an optical element can be arranged in the connecting zone or the connecting zone can be embodied as an optical element, for example in order to modify the beam guidance and/or light steering by geometry or by matching of refractive powers.

Further, to protect the diffuser main body, a jacket is advantageously provided, the latter surrounding the diffuser main body at least in part or in sections or else in full in a preferred embodiment, wherein it may be advantageous if at least the connecting zone between the diffuser main body and light guide is additionally also surrounded. Using this, the mechanical resilience of the light guide/diffuser main body connection can be increased further. Advantageously, the light guide does not have a buffer layer in this region, and so this zone can be protected by such a jacket without requiring a so-called recoating process for mechanical protection.

In a particularly advantageous embodiment, the diffuser main body no longer has any unprotected surfaces, neither in the direction or region of the input coupling point and nor in the opposite direction, neither of which are covered by the protecting jacket. This offers an additional and solid protection of the surface of the diffuser main body and/or the input coupling point, for example from external damage to the surface of the diffuser main body such as cracks or scratches as a consequence of use, which could lead to an altered emission characteristic and which can therefore be very disadvantageous for the envisaged applications. This can increase the longevity of the illumination system.

In a further particularly advantageous embodiment, the jacket surrounds at least the connecting zone between diffuser main body and light guide and thus ensures a particularly high stability of the connection since the outer region of the connection is protected particularly well from external influences. A jacket which at least protects and surrounds the connecting zone between the diffuser main body and the light guide offers a further great advantage. Since the light guide has no buffer layer here, this region is susceptible to corrosion, for instance in connection with water vapor in the atmosphere or as a result of contacts with liquid or moisture during use. A moisture-tight jacket especially in this region accordingly also safely protects the light guide in the contact region with the diffuser main body from corrosion and therefore likewise increases the longevity of the illumination system.

In this case, the jacket can comprise a layer that is transparent or translucent to light emitted laterally from the diffuser element and consists of liquid silicone, thermoplastic polymer, hot melt adhesive, 2-component adhesive or sol-gel glass, of a shrink tubing or of additionally applied transparent or translucent attachment elements, which surround the diffuser main body and/or the transition point between diffuser main body and light guide. A varnish layer additionally containing light-scattering pigments, for example in the form of titanium oxide, aluminum oxide or calcium carbonate, was also found to be advantageous. This can additionally achieve a homogenization of the emission. By way of example, this layer can be applied as a dipped layer or by coating the surface.

An inclusion with a glass that melts at comparatively low temperatures, which has a low processing temperature of preferably less than 500° C., by preference less than 400° C. and particularly preferably less than 300° C., is also conceivable. When selecting a suitable glass, care has to be taken that the softening the processing temperature of the selected glass is lower than that of the diffuser element or of the diffuser main body. This ensures that no unwanted modifications can occur, for instance in relation to the scattering centers and hence the emission characteristic, when applying the glass that melts at low temperatures to the diffuser main body. It is advantageous if the processing temperature of the material to be applied is at least 50 K, preferably at least 100 K lower softening temperature of the diffuser element. What should be taken into account here is that the diffuser element can comprise different materials, for instance also the core and/or the cladding of the light guide, and the diffuser main body. Therefore, these possibly different softening temperatures are advantageously also considered.

In this case, the jacket has a certain minimum and maximum thickness such that, firstly, there is sufficient protection for the diffuser main body and, secondly, the diffuser element overall does not become too large for the planned uses. A jacket that has been formed too thick can also lead to unwanted attenuation of the emission.

Typical layer thicknesses of a varnish layer are approximately 10 µm to 100 µm, wherein multi-ply layers can also be provided Typical thicknesses of a tubing start at approximately 5 µm and go up to approximately 500 µm.

Preferably, the diffuser element comprises at least one scattering element or is formed as a scattering element and comprises at least one scattering center. In the present invention, the radial, spherical emission characteristic is brought about by scattering of the light, which was introduced into the diffuser main body, in the scattering region where the scattering occurs.

The scattering centers are responsible for the scattering; these are embedded in the scattering region. Within the sensor the invention, scattering centers are, in principle, all particles and/or material agglomerations and/or inhomogeneous regions that are able to scatter light, regardless of form, material and/or size. The scattering centers can develop the scattering effect both by classical scattering, in particular Raleigh and/or Mie scattering, and by diffraction and/or reflection, as well as multiple processes of these mechanisms among themselves. Their function is merely to deflect incident light, either individually or in their sum.

Optically active pigments are also conceivable, for example illuminants, i.e., substances that can exhibit luminescence as a consequence of their excitation. By way of example, these can comprise certain phosphors which can convert irradiated light at a certain wavelength into light at a different wavelength and can emit the latter. In addition to these substances characterized by the phosphorescence, use can also be made, for example, of substances that exhibit fluorescence. Such materials are also known as organic or inorganic phosphors, which can be embedded in a matrix of inactivity material, for example plastics (epoxy and silicone), glass, glass ceramic or glass-like substances or ceramics, or as ceramic converters, so-called optoceramics, which form phosphor. Using these, it is also possible to realize emissions with superposed spectra of the wavelength radiated in and the emitted wavelength.

A plurality of scattering centers can be arranged in the volume in a certain pre-definable geometric arrangement, preferably around the center of the diffuser main body.

Different arrangements and/or concentrations of the scattering centers in the volume of the diffuser main body are conceivable.

Thus, in a preferred embodiment, provision can be made for the scattering centers to be arranged in a regular structure and with a homogeneous concentration in the volume of the diffuser main body, preferably around the center; this leads to uniform concentration in the volume. The density of the scattering centers can be set by chemical or thermal processes such that it is possible to set a homogeneous distribution, or else an inhomogeneous distribution, over the entire volume.

In a further embodiment, a composite body can also be provided as a scattering element; it comprises at least one strongly scattering material, for example a highly doped white glass. The scattering can be set locally by scattering centers embedded in a targeted manner.

In another embodiment, provision can also be made for a core zone around the center of the diffuser main body to have no scattering centers or a significantly reduced number of scattering centers as per unit volume in relation to the number of scattering centers per unit volume outside of the core zone, and hence for the scattering centers to be predominantly arranged outside of this core zone. In this case, the core zone preferably relates to a volume surrounding the center and having an extent that is no greater than half of the greatest extent of the diffuser main body in one direction. What this can achieve is that input-coupled light, which is generally coupled in with a low NA (<0.3, typically around 0.2), is not immediately scattered at the scattering centers but is emitted homogeneously with the same intensity in spherical fashion.

In this embodiment, the scattering center density in the region near the surface of the diffuser main body accordingly differs from that in region of the diffuser main body close to the center; preferably, the scattering center density in the region close to the surface is greater in this case than in the region close to the center and particularly preferably there is a scattering center density gradient. Here, the term scattering center density means the density, i.e., the number of scattering centers per unit volume.

The scattering centers include, inter alia, pores, particles, crystallites, polycrystallites, porous and/or pigmented and/or optically active pigments, e.g., in the form of phosphors and/or colored regions, for example colored particles, colored crystallites or colored pigments, or colorations of the glass or inhomogeneities in the form of refractive index variations or any combination of such scattering centers, wherein the inhomogeneities of the inorganic material comprise phase separations, demixing and/or particulate inclusions, seeds and/or crystallites.

In this case, combinations of the scattering centers mentioned in exemplary fashion above can advantageously also be present in the inorganic material. The inhomogeneities of a glass or glass ceramic which can form the scattering elements in the case of glass or glass ceramic matrix solutions, comprise, for example, phase separations, demixing and/or particulate inclusions, seeds and/or crystallites.

In the case of glass or glass ceramic as inorganic material for the diffuser main body, scattering particles can preferably be embedded into the glass or the glass ceramic as scattering centers, or else the scattering centers are formed by inhomogeneous regions of the glass or the glass ceramic in which they are embedded.

Such scattering centers on the basis of scattering particles in the glass or in a glass ceramic or inhomogeneous regions of the glass or the glass ceramic and the underlying methods for production are described, for example, in the document WO 2009/100834 by the applicant, the content of which, in its entirety, is herewith made part of the subject matter of the present invention.

If scattering particles are used as scattering centers, use is preferably made of scattering particles whose melting point is higher than the melting point of the glass or the glass ceramic in which they are embedded. Since the scattering particles do not alter at least their scattering properties during the production process, their selection is simplified and they can be purchased accordingly as raw material.

Preferably, the scattering particles have a diameter between 10 nm and 5000 nm, particular preferably between 100 nm and 1200 nm. For scattering particles that are not round, the diameter is understood to mean their maximum extent within the meaning of the invention. This also applies to size specifications at other points, wherein the specification of the diameter should likewise be understood to mean a maximum extent in one direction if the underlying object does not have a diameter. Scattering particles with the aforementioned dimensions are for example well-suited in combination with a white glass as a material for the diffuser main body.

These dimensions can also apply to other forms of scattering centers, for example for pores, crystallites or inhomogeneities, wherein inhomogeneities that have arisen due to phase separation or demixing tend to be able to have relatively small diameters, for example ranging from 10 nm to 1000 nm or from 100 nm to 800 nm. Thus, for instance, 200 nm to 700 nm 200 nm to 500 nm are assumed to be advantageous dimensions of particles or pores in a borosilicate glass.

The scattering particles can be chosen from a multiplicity of materials. Preferably, they substantially consist of $SiO_2$ and/or BaO and/or MgO and/or BN and/or AlN and/or SN and/or $ZrO_2$ and/or $Y_2O_3$ and/or $Al_2O_3$ and/or $TiO_2$ and/or Ru and/or Os and/or Rh and/or Ir and/or Ag and/or Au and/or Pd and/or Pt and/or diamond-like carbon and/or glass ceramic particles. Mixtures of scattering particles made of different materials, compounds and/or conglomerates thereof, or else scattered particles that have been sintered and/or fused together are likewise conceivable and also comprised by the invention, just like the metallic components of the aforementioned oxides and nitrides on their own.

The efficiency of the output coupling from the scattering region in addition to the scattering property of the scattering particles as intrinsic parameter also depends on the concentration of the scattering particles in the scattering region. By choosing the concentration of the scattering centers in the scattering region, it is possible to scale the emission.

Therefore, one embodiment of the invention provides for the scattering centers to be formed by the scattering particles, with the concentration of the scattering particles in the scattering region ranging from 10 ppm to 1000 ppm and preferably from 20 ppm to 100 ppm. Here, the specification of concentration in ppm refers to the proportion of the scattering particles in relation to the proportions by mass of the constituent parts of the respective inorganic material in which the scattering particles are embedded. Even in the case of different types of scattering centers, for example pores, inhomogeneities in the material or crystallites in the case of a glass ceramic, these concentrations were found to be helpful.

Byway of example, if inhomogeneous regions of the glass or of the glass ceramic serve as scattering centers, an alternative embodiment of the invention arises, in which the inhomogeneous regions are preferably formed by phase separation and/or demixing of the components of the class or of the glass ceramic, in which they are embedded.

According to the invention and as described above, the diffuser main body itself comprises an inorganic material, in particular a glass, a glass ceramic, a quartz glass or a glass-like substance or a composite substance made of the aforementioned materials. However, glasses, multicomponent glasses or glass ceramics or composite substances made of these materials are particularly preferably used since these facilitate simpler and better setting of the emission characteristic.

A glass or a glass ceramic is particularly suitable as a material for the diffuser main body since, in comparison with plastics, for example, it is substantially more robust and, especially, more stable from a thermal point of view, and so even relatively high laser powers are able to be applied.

For the envisaged uses, a material with a neutral behavior in relation to electromagnetic radiation in the wavelength range which is selected for the envisaged use and which, accordingly, is preferably emitted by the light source can be considered to be particularly suitable for the diffuser main body. The wavelength range of electromagnetic radiation relevant to the invention lies between approximately 0.4 μm and approximately 2.2 μm. For phototherapy applications, typical ranges are in the visible spectrum, particularly in the red spectral range between 600 nm and 700 nm, in particular at 690 nm, or in the NIR range between 700 nm and 1000 nm. EVLT applications in this case tend to target wavelengths between 800 nm and 2.2 μm, typically in a range from 980 nm to 1100 nm, around 1500 nm, and regions between 1.9 μm and 2.2 μm.

According to the invention, provision is made in a first embodiment for a glass with or without own coloration to be chosen for the diffuser main body, the desired wavelength of electromagnetic radiation not being absorbed in said glass. This might be a white glass which comprises white pigments in order to bring about a whitish color impression.

In a particularly preferred embodiment, the diffuser main body comprises a silicate white glass. The latter has an extreme scattering effect. Preferably, this is an As—Pb-containing silicate glass. Such a glass is a silicate glass which contains lead (Pb) and arsenic (As). In the case of inhomogeneous regions as a scattering element, these inhomogeneous regions can have an increased content of lead and/or arsenic in relation to the surrounding glass. Alternatively, it is naturally also possible for scattering elements, for instance scattering particles, to be embedded and to form the scattering centers.

A particularly suitable glass for the diffuser main body is a Na—Al—K—As—Pb silicate glass. The latter can comprise at least 25% by weight of lead oxide in the glass, preferably at least 30% by weight of lead oxide. Inhomogeneous regions which represent scattering elements, for example drop-shaped demixing zones with an elevated lead content, then form lead arsenate with, e.g., 38% by weight of lead, or more, wherein these demixing zones can have a diameter between 100 nm and 600 nm. The Na—Al—K—As—Pb silicate glass can comprise 3% by weight or more of arsenic oxide. A possible composition of a Na—Al—K—As—Pb silicate glass suitable according to the invention is shown in table 1.

TABLE 1

Composition of a Na—Al—K—As—Pb silicate glass suitable according to the invention

| | Ma.-% Inhomogeneous | Ma.-% homogeneous | M | mol/100 g inhomogeneous | mol/100 g homogeneous | mol-% inhomogeneous | mol-% homogeneous |
|---|---|---|---|---|---|---|---|
| SiO2 | 47.1 | 47.6 | 60.084 | 0.7839 | 0.7922 | 69.09 | 69.77 |
| Al2O3 | 1.7 | 1.7 | 101.961 | 0.0167 | 0.0167 | 1.47 | 1.47 |
| PbO | 34.4 | 34.4 | 223.199 | 0.1541 | 0.1541 | 13.58 | 13.57 |
| Na2O | 3.6 | 3.4 | 61.979 | 0.0581 | 0.0549 | 5.12 | 4.83 |
| K2O | 6 | 5.6 | 94.195 | 0.0637 | 0.0595 | 5.61 | 5.24 |
| CaO | 1.42 | 1.4 | 56.079 | 0.0253 | 0.0250 | 2.23 | 2.20 |
| As2O3 | 4.9 | 5 | 197.841 | 0.0248 | 0.0253 | 2.18 | 2.23 |
| Fe2O3 | 0.03 | 0.03 | 159.691 | 0.0002 | 0.0002 | 0.02 | 0.02 |
| P2O5 | 1 | 1 | 141.943 | 0.0070 | 0.0070 | 0.62 | 0.62 |
| ZnO | 0.07 | 0.05 | 81.379 | 0.0009 | 0.0006 | 0.08 | 0.05 |
| Sum | 100.22 | 100.18 | | 1.1347 | 1.1354 | 100.00 | 100.00 |

In a particularly preferred embodiment, a Na—Al—K—As—Pb silicate glass with 30% by weight of the lead oxide and 3% by weight of arsenic oxide is chosen as a colored glass with a white impression. No scattered particles are introduced; instead the colored glass that is transparent and colorless at the outset demixes during the production, and so demixing zones with a diameter having a size of 50 nm to 500 nm arise and are distributed uniformly. These demixing zones are lead arsenate and comprise a substantially higher refractive index than that of the basic glass, as a result of which the scattering effect arises. This colored glass which is now white and opaque can then be processed further to form the desired geometries for the diffuser main body, i.e., a spherical geometry, for example.

Naturally, other glasses, including lead-free glasses or heavy metal-free glasses or low heavy metal content glasses are also possible and suitable for the invention.

Examples of such glasses for the diffuser main body from the range of lead-free tin silicate glasses or alkali tin silicate glasses contain the following components (specified in percent by weight on an oxide basis):

TABLE 2

Composition range of a lead-free tin silicate glass in % by weight

| | from | to |
|---|---|---|
| B$_2$O$_3$ | 0 | 24 |
| SiO$_2$ | 23 | 62.1 |
| Al$_2$O$_3$ | 0 | 10 |
| Li$_2$O | 0 | 10 |
| Na$_2$O | 0 | 18.5 |
| K$_2$O | 0 | 25.7 |
| BaO | 0 | 57.8 |
| ZnO | 0 | 40 |
| La$_2$O$_3$ | 0 | 25 |
| ZrO$_2$ | 0 | 10 |
| HfO$_2$ | 0 | 14.2 |
| SnO$_2$ | >0 | 2 |
| MgO | 0 | 8 |
| CaO | 0 | 8 |
| SrO | 0 | 24.4 |
| Ta$_2$O$_5$ | 0 | 22 |
| Y$_2$O$_3$ | 0 | 11.9 |

TABLE 2-continued

Composition range of a lead-free tin silicate glass in % by weight

|  | from | to |
|---|---|---|
| $Rb_2O$ | 0 | 15 |
| $Cs_2O$ | 0 | 21 |
| $GeO_2$ | 0 | 7.5 |
| F | 0 | 2 |
| $\Sigma R_2O$ | 5 | 20 |
| $\Sigma$ MgO, CaO, SrO, ZnO | 20 | 42 |

It is possible to use a Na—Al—K—Ca—Zn silicate class which is lead-free and arsenic-free, which may be advantageous from environmental points of views. In this case, too, it is possible to form, e.g., spherical pores in the volume, which represent calcium-rich deposits in this case. The scattering centers of formed by these inhomogeneities in the glass. The achievable size of the pores is up to 500 nm. The calcium-rich deposits in these demixing zones consist of $CaF_2$.

Further suitable glasses include the N—BK7 type classes, optical borosilicate crown glass by the applicant or borosilicate glass.

In this context, a further material very suitable for the invention should be mentioned, for example, which material is suitable for inducing Mie scattering. Mie scattering means scattering that arises when a defect, for instance an inhomogeneity, is comparable in terms of size with the current wavelength, i.e., greater than 10% of the wavelength.

The production and various configurations of such materials are described in the document WO 2014/165048 A1 or DE 11 2014 001 293 T5 by the applicant, the content in this respect, in its entirety, is likewise herewith made part of the subject matter of the present invention.

According to the invention, the diffuser main body can be produced from porous or phase-separated glass, which is formed to optimize a scattering in the desired emission direction while, at the same time, the desired solid angle of the scattered light in the desired emission direction is achieved.

Therefore, a scattering diffuser main body is provided in accordance with a further embodiment of the invention, said diffuser main body being formed from a glass system that runs through a phase separation such as, e.g., the conventional borosilicate glass system; the $K_2O$—$SiO_2$, $K_2O$—$Li_2O$—$SiO_2$, $K_2O$—$Na_2O$—$SiO_2$ and $K_2O$—$BaO$—$SiO_2$ systems (Kawamoto and Tomozawa, 1981, J. Amer. Ceram. Soc., vol. 64 (5), 289-292); the MgO—$Al_2O_3$—$SiO_2$ system (Zdaniewski, 1978, J. Amer. Ceram. Soc., vol. 61 (5-6), pages 199-204) and the $CdF_2$—LiF—$AlF_3$—$PbF_2$ system (Randall et al., 1988, J. Amer. Ceram. Soc., vol. 71 (12), pages 1134-1141).

These can be subjected to the phase separation by means of a controlled thermal treatment, wherein the glass composition separates into two phases, and optionally a further intervention for producing an open porosity within the glass by a leaching step in order to obtain a glass with pores of the order of 200 to 700 nm, for example 200 to 500 nm, preferably 300 to 500 nm, particularly preferably 300 to 450 nm, with a number density of approximately $10^8$ to $10^{12}$ $mm^{-3}$, preferably $10^9$ to $10^{11}$ $mm^{-3}$, particularly preferably $10^{10}$ to $10^{11}$ $mm^{-3}$.

According to a further aspect of the invention, a diffuser main body with the scattering element is provided, said diffuser main body being produced by melting a borosilicate glass, preferably an alkaline borosilicate glass, which, after being slowly cooled for stress relief is subjected to phase separation using a well-controlled thermal treatment, wherein the composition separates into silicate-rich phase and are boron-rich phase, and optionally subjected to a further intervention for producing porosity within the glass by way of an acid leaching step and a pore-cleaning caustic leaching step, in order to obtain a glass with pores of the order of 200 to 700 nm, for example 200 to 500 nm, preferably 300 to 500 nm, particularly preferably 300 to 450 nm, with a number density of approximately $10^8$ to $10^{12}$ $mm^{-3}$, preferably $10^9$ to $10^{11}$ $mm^{-3}$, particularly preferably $10^{10}$ to $10^{11}$ $mm^{-3}$.

According to a further aspect of the invention, a diffuser element is provided, comprising at least one optical fiber and at least one Mie scattering diffuser main body for dispersing light emitted by the at least one optical fiber, wherein the at least one Mie scattering diffuser main body comprises a phase separated or porous glass (such as borosilicate glass, for example, preferably an alkali borosilicate glass) with dispersive phase particles with the particle size of 200 to 700 nanometers, for example 200 to 500 nanometers or pores with the size of 200 to 700 nanometers, for example 200 to 500 nanometers, with the number density of $10^8$ bis $10^{12}$ $mm^{-3}$.

According to a further aspect of the invention, an illumination system is provided, comprising an optical fiber or an optical fiber bundle and an optically scattering element which is attached to the distal end of the optical fiber or the optical fiber bundle for the purposes of scattering light that is emitted by the distal end of the optical fiber or optical fiber bundle, wherein the optically scattering element comprises a phase separated or porous glass (such as borosilicate glass, for example, preferably an alkali borosilicate glass) with dispersive phase particles with the particle size of 200 to 700 nanometers, for example 200 to 500 nanometers or pores with the size of 200 to 700 nanometers, for example 200 to 500 nanometers, with the number density of $10^8$ bis $10^{12}$ $mm^{-3}$.

The references to particle size of, e.g., 200 to 700 nanometers and a pore size of, e.g., 200 to 700 nanometers should mean that the relevant pores or particles have an actual diameter of 200 to 700 nanometers. Thus, for example, in the diffuser main body according to the invention, the amount, i.e., the number density, of particles or pores with an actual diameter of, e.g., 200 to 700 nanometers will be $10^8$ to $10^{12}$ $mm^{-3}$, (preferably $10^9$ to $10^{11}$ $mm^{-3}$, particularly preferably $10^{10}$ to $10^{10}$ $mm^{-3}$).

The diffuser main body can comprise particles or pores with an actual diameter outside of the range from 200 to 700 nanometers; however, the number of particles or pores with an actual diameter of 200 to 700 nanometers will be $10^8$ to $10^{12}$ $mm^{-3}$, (preferably $10^9$ to $10^{11}$ $mm^{-3}$, particularly preferably $10^{10}$ to $10^{11}$ $mm^{-3}$).

According to a further aspect of the invention, a method for producing a diffuser element with a Mie scattering diffuser main body is provided, the method comprising: producing a Mie scattering optical element by subjecting a glass (such as a borosilicate glass, for example, preferably an alkali borosilicate glass) slowly cooled for stress relief to a phase separation using a controlled thermal treatment and optionally subjecting the phase separated glass to acid leaching in order to produce pores and caustic leaching in order to clean the resultant pores, and attaching the resultant Mie scattering optical element to the end of an optical fiber or to the end of a bundle optical fibers.

According to a further aspect, a method is provided for diffusing or scattering light, which is implemented by transmitting the light through an optically scattering element, preferably through the diffuser main body, comprising a phase separated or porous glass (for example borosilicate glass or an alkali borosilicate glass) with dispersive phase particles with the particle size of 200 to 700 nanometers, for example 200 to 500 nanometers or pores with the size of 200 to 700 nanometers, for example 200 to 500 nanometers, with the number density of $10^8$ bis $10^{12}$ mm$^{-3}$.

By way of example, the optically scattering element can be produced by melting a borosilicate glass, preferably an alkali borosilicate glass, which is subjected to a phase separation using a well-controlled thermal treatment after it has been cooled slowly for stress relief and which is optionally subjected to a further intervention for producing open porosity within the glass by way of an acid leaching step and a pore-cleaning caustic leaching step, in order to obtain a glass that has pores of the order of 200 to 700 nanometers, for example 200 to 500 nanometers, preferably 300-500 nm, in particular 350-400 nm, with a number density of approximately $10^8$ to $10^{12}$ mm$^{-3}$, preferably $10^9$ to $10^{11}$ mm$^{-3}$, particularly preferably $10^{10}$ to $10^{11}$ mm$^{-3}$.

According to the invention, a thermal treatment of the borosilicate parent glass, by preference an alkali borosilicate glass, preferably in one of the compositions listed below, induces a glass-in-glass phase separation. The phases are defined as the silicate rich phase and a boron rich phase. After passing through the heat treatment, the parent glass can then be chemically leached. If the parent classes chemically leached, the host phase or the bulk phase is considered to be the silicate-rich phase and the pores which result from the removal of the boron-rich phase are considered to be the scattering feature.

To obtain a glass having such a combination of features in the nano range of the order of 200 to 700 nm, e.g., 200-500 nm, with a number density of approximately $10^8$ to $10^{12}$ mm$^{-3}$, the glass should be subjected to a well-controlled thermal treatment profile. In respect of commercially available products, SCHOTT AG, Mainz, has made available, e.g., a porous glass, sold under the trade name CoralPor™, for instance for application and chromatography media, reference electrode crossings, as a host material for senses and as an additive (filler) and coatings (see James et al., US 2013/0017387). During production, CoralPor™ porous glass is subjected to a carefully controlled thermal treatment in order to induce a glass-in-glass phase separation. Ultimately, this thermal treatment determines the final size of the scattering features present in the material. This leads to it being possible to manipulate the production method in order to produce CoralPor™ porous glass in a form which meets the desired criteria, i.e., 200 to 700, e.g., 200-500 nm features with a number density of $10^8$ to $10^{12}$ mm$^{-3}$.

According to the invention, the scattering optical elements can be produced by, for example, melting a borosilicate glass, preferably an alkali borosilicate glass which, after having been cooled slowly for stress relief, is subjected to a phase separation by means of the thermal treatment with a controlled temperature/time profile in the temperature range from 500-800° C., such as for example 600-800° C., preferably 650-750° C., more preferably 700-725° C., for a time interval of, for example, 1 to 150 hours, such as, for example, 24 to 48 hours or 48 to 80 hours. By way of example, for a given composition, the thermal treatment used to obtain features in the nano range of approximately 200 nanometers can comprise a duration of 20-26 hours at 700° C. The cooling phase also plays a role here; it should likewise be controlled accordingly in respect of its temperature/time profile in order to obtain an optimal or undesired scattering effect.

The conditions can be set on the basis of the utilized melting parameters (i.e., temperature and quenching method) and composition. In general, the employed method depends on the desired phase growth. By way of example, in general, an elevated temperature for a longer duration within the phase separation region leads to larger feature dimensions, although the dimensions of the features will also depend on the specific composition.

This thermal treatment method can be considered to be complete for some applications. Expressed differently, some applications require no further method steps in order to achieve the desired results of 200 nm to 700 nm, e.g., 200-500 nm features with a number density of approximately $10^8$ to $10^{12}$ mm$^{-3}$.

Byway of example, the base glass can be a borosilicate glass having suitable silicon dioxide and borate contents so that the phase separation occurs, and having a sufficient borate content to obtain the desired number density of pores in the nanometer range. Preferably, the borosilicate glass comprises at least some alkali metal oxides. Byway of example, the borosilicate glass composition according to one embodiment of the invention comprises (based on % by weight):

$B_2O_3$ 15.00-40.00
$SiO_2$ 45.00-80.00
$R_2O$ 0.0-20.0
R'O 0.0-20.00
R"$O_2$ 0.0-10.00
$Al_2O_3$ 0.0-10.00
where $R_2O$ is the sum of $Li_2O$, $Na_2O$, $K_2O$, $Rb_2O$ and $Cs_2O$ (and preferably greater than 0), R'O is the sum of BaO, CaO, MgO, SrO, PbO and ZnO and R"$O_2$ is the sum of $TiO_2$, $ZrO_2$ and $HfO_2$.

A further borosilicate glass composition suitable for the invention is specified below (based on % by weight):
65% to 85% $SiO_2$
6% to 15% $B_2O_3$
3% to 9% alkali oxides (sodium oxide $Na_2O$; potassium oxide $K_2O$)
1% to 8% $Al_2O_3$
0% to 5% earth alkali oxide (CaO, MgO, . . . )

In view of the ranges specified in this description, all ranges comprise at least the two endpoints of the ranges and all values between the two endpoints. By way of example, a range from 1 to 10 should be understood to mean that it expressly discloses the values of, for instance, 1.0, 1.5, 2.0, 2.8, 3.0, 3.1, 4.0, 4.2, 5.0, 5.3, 6.0, 7.0, 7.7, 8.0, 9.0, 9.9 or 10.0.

In the borosilicate glass, $SiO_2$ functions as a primary network former. Accordingly, according to a further aspect of the invention, the borosilicate glass composition comprises 45.00-80.00% by weight of $SiO_2$, for example 45.00-75.00% by weight of $SiO_2$ or 45.00-70.00% by weight of $SiO_2$ or 45.00-65.00% by weight of $SiO_2$ or 45.00-60.00% by weight of $SiO_2$ or 50.00-60.00% by weight of $SiO_2$.

In the borosilicate glass, $B_2O_3$ functions as a network former and as primary form of the features in the nano range of the resultant face separated/porous glass. Accordingly, according to a further aspect of the invention, the borosilicate glass composition comprises 15.00-40.00% by weight of $B_2O_3$, for example 20.00-35.00% by weight of $B_2O_3$ or 20.00-30.00% by weight of $B_2O_3$.

According to a further aspect, the borosilicate glass composition comprises 0.00-20.00% by weight of $R_2O$ (preferably >0.00-20.00% by weight of $R_2O$), where $R_2O$ is the sum of $Li_2O$, $Na_2O$, $K_2O$, $Rb_2O$ and $Cs_2O$, for example 1.00-15.00% by weight of $R_2O$ or 1.00-10.00% by weight of $R_2O$ or 2.00-8.00% by weight of $R_2O$.

According to a further aspect, the borosilicate glass composition comprises 0.00-20.00% by weight of R'O (the sum of BaO, CaO, MgO, SrO, PbO and ZnO), for example 1.00-15.00% by weight of R'O or 1.00-10.00% by weight of R'O or 2.00-8.00% by weight of R'O. The R'O metal oxides can be used to set the refractive index in each phase.

According to a further aspect, the borosilicate glass composition comprises 0.00-10.00% by weight of $R''O_2$ (the sum of $TiO_2$, $ZrO_2$ and $HfO_2$), for example 0.00-8.00% by weight of $R''O_2$ or 1.00-8.00% by weight of $R''O_2$ or 0.00-5.00% by weight of $R''O_2$ or 1.00-5.00% by weight of $R''O_2$. These metal oxides can be used to increase the chemical stability and can be used to set the refractive index of each phase.

In the borosilicate composition, $Al_2O_3$ usually acts as a network code former and can also be used to increase the chemical stability. Accordingly, according to a further aspect, the borosilicate glass composition of the invention comprises 0.00-10.00% by weight of $Al_2O_3$, for example 0.00-8.00% by weight of $Al_2O_3$ or 1.00-8.00% by weight of $Al_2O_3$ or 0.00-5.00% by weight of $Al_2O_3$ or 1.00-5.00% by weight of $Al_2O_3$ or 2.50-5.00% by weight of $Al_2O_3$.

According to a further aspect, the glass can be a glass according to the glass composition described in James et al. (US 2013/0017387). This glass composition comprises (on the basis of % by weight): 40-80% $SiO_2$, 5-35% $B_2O_3$ and 1-10% $Na_2O$, preferably 45-65% $SiO_2$, 20-30% $B_2O_3$ and 2-8% $Na_2O$ and particularly preferably 50-55% $SiO_2$, 25-27% $B_2O_3$ and 5-7% $Na_2O$. As disclosed in document US, the glass can comprise further constituents, for example $ZrO_2$, $TiO_2$, $Al_2O_3$, CaO and/or ZnO, and optionally further constituents, e.g., oxides of Mg, Fe, Mn, Ce, Sn, etc.

Tables 3-6 below represent further examples of suitable base glasses A to T for the use according to the invention.

In general, what is decisive that in a separation, phases with a higher refractive index are present in addition to phases with a lower refractive index in order to obtain a scattering effect

TABLE 3

Glass compositions based on % by oxide weight

| Oxide | A | B | C | D | E | F |
|---|---|---|---|---|---|---|
| $SiO_2$ | 52.40 | 52.77 | 50.93 | 56.85 | 54.85 | 56.85 |
| $B_2O_3$ | 25.99 | 25.87 | 25.73 | 30.31 | 30.31 | 30.31 |
| $Al_2O_3$ | 3.42 | 3.41 | 3.39 | | | |
| $Na_2O$ | 5.92 | 5.89 | 5.86 | 6.90 | 6.90 | 6.90 |
| CaO | 5.14 | 5.12 | 5.09 | | | |
| ZnO | | | | 3.00 | 4.00 | 2.00 |
| $TiO_2$ | 2.00 | | 2.00 | | | 2.00 |
| $ZrO_2$ | 5.14 | 6.94 | 7.00 | 3.00 | 4.00 | 2.00 |

TABLE 4

Glass compositions based on % by oxide weight

| Oxide | G | H | I | J | K | L |
|---|---|---|---|---|---|---|
| $SiO_2$ | 54.65 | 58.92 | 57.68 | 58.69 | 57.69 | 60.19 |
| $B_2O_3$ | 30.31 | 28.41 | 27.81 | 28.30 | 27.82 | 29.02 |
| $Al_2O_3$ | | | | | | |
| $Na_2O$ | 6.90 | 6.47 | 6.33 | 6.44 | 6.33 | 6.61 |
| CaO | | | | | | |
| ZnO | 3.00 | 3.10 | 4.09 | 2.06 | 3.05 | 2.10 |

TABLE 4-continued

Glass compositions based on % by oxide weight

| Oxide | G | H | I | J | K | L |
|---|---|---|---|---|---|---|
| $TiO_2$ | 2.00 | | | 1.33 | 1.97 | |
| $ZrO_2$ | 3.00 | 3.09 | 4.09 | 3.18 | 3.14 | 2.80 |

TABLE 5

Glass compositions based on % by oxide weight

| Oxide | M | N | O | P | Q | R |
|---|---|---|---|---|---|---|
| $SiO_2$ | 56.86 | 57.47 | 53.28 | 50.61 | 52.70 | 52.12 |
| $B_2O_3$ | 27.43 | 27.72 | 26.43 | 26.23 | 26.14 | 25.86 |
| $Al_2O_3$ | | | | | | |
| $Na_2O$ | 6.24 | 6.31 | 6.02 | 5.97 | 5.95 | 5.89 |
| CaO | | | | | | |
| ZnO | 5.41 | 5.49 | 5.23 | 5.20 | 5.18 | 5.12 |
| $TiO_2$ | | | 2.00 | 6.98 | 2.00 | 2.01 |
| $ZrO_2$ | 4.03 | 3.01 | 7.03 | 5.00 | 8.02 | 8.99 |

TABLE 6

Glass compositions based on % by oxide weight

| Oxide | S | T |
|---|---|---|
| $SiO_2$ | 60.19 | 54.15 |
| $B_2O_2$ | 29.02 | 26.11 |
| $Al_2O_3$ | | 3.45 |
| $Na_2O$ | 6.61 | 5.68 |
| CaO | | |
| ZnO | 2.10 | 5.17 |
| $TiO_2$ | | |
| $ZrO_2$ | 2.08 | 5.18 |

A diffuser main body and is particularly preferred in respect of its production process arises if the diffuser main body is formed from borosilicate glass, tin silicate glass or alkali tin silicate glass and the scattering elements are formed from white glass.

According to yet further embodiment of the invention, a diffuser main body is provided, in which the diffuser main body comprises a glass ceramic or is manufactured from a glass ceramic material. The use of a glass ceramic material for the diffuser main body offers the advantage that the diffuser main body as a whole is identifiable at least in part or in sections in an x-ray image, and consequently it is possible to determine the position of the diffuser in the body of a patient.

Moreover, glass ceramic material is extremely thermal shock stable and has a high spectral transmission up to wavelength of approximately 2.5 μm, making it particularly interesting to the invention. Here, a glass-ceramic material can be used not only for the diffuser main body but also is a scattering element, for example a keatite glass ceramic which can be produced by a suitable heat treatment process from the high quartz mixed crystal glass ceramic. Furthermore, cordierite glass ceramics or magnesium aluminum silicate glass ceramics are also suitable as diffuser main body and/or scattering element.

A particularly suitable glass ceramic materials for the diffuser main body and/or the scattering centers are represented by the glass ceramics based on lithium aluminosilicate glass ceramics (LAS glass ceramics). In the case of glass ceramics based thereon, it is possible by means of a heat treatment process to choose as desired between a cleared transparent high quartz mixed crystal phase and an opaque keatite phase of the material, and so these appear particularly suitable. Expressed differently, a glass ceramic, preferably a lithium aluminosilicate glass ceramic, is produced, in which the crystallite size and the distribution thereof in the volume can be set in a targeted fashion by a targeted temperature/time application over the crystal formation and the crystal growth, and wherein the crystallites act as scattering centers in the glass ceramic.

Byway of example, such glass ceramic materials are able to be obtained for cooker tops under the trade name CERAN CLEARTRANS® or for fireplace viewing panels under the trade name ROBAX® from Schott AG, Mainz. Such glass ceramics and production methods are also specified, for example, in the document EP 1 266 543 A1 by the applicant, the content of which, likewise in its entirety, is herewith made part of the subject matter of the present invention.

In principle, it is also possible to use an x-ray opaque glass or a corresponding transparent glass ceramic for the diffuser main body of for the embedded scattering elements and/or for the jacket.

In view of the wavelength range from 0.4 µm to approximately 2.2 µm, for example when using the illumination system for endovenous laser therapy (EVLT), use can also be made of specific IR transparent glasses, as are known by the trade names N-PK52a, a phosphate crown glass, or IRG7, a lead silicate glass, all of which can be obtained from Schott AG, Mainz.

The scattering centers in the diffuser main body can also be influenced retrospectively in respect of the scattering effects if the diffuser main body is subjected to a subsequent heat treatment, in particular a gradient heat treatment. Thus, for example, a demixing process in the white the glass rods used as scattering centers, for example, can be varied byway of such a gradient heat treatment. In the case of glass ceramic-based scattering centers, the crystal formation and the crystal growth or the crystallite size and the distribution of thereof in the volume of the diffuser main body can be influenced.

A diffuser main body obtained in this manner can then be connected to the light guide by means of splicing or adhesive bonding using a refractive index-matched adhesive.

To reduce unwanted scattering, stray light effects and/or light reflections, in particular in the transition region from the light guide to diffuser main body, provision can be made in a further preferred embodiment variant for the scattering centers in the direct vicinity of the input coupling face of the diffuser main body to have a reduced scattering effect in relation to the scattering effect in the remaining volume of the diffuser main body.

Byway of example, this can be obtained by an additional temperature application, for example during the splicing procedure for the diffuser main body and light guide. As a result, demixing (for example phase separation, devitrification) present in scattering elements made of white glass can be locally modified at least in part, for example also be reduced or be undone again. As a result of the latter, the scattering effect is reduced in this region.

In all the materials and methods for producing the diffuser main body listed above, a wavelength-dependent scattering effect can be obtained by means of a certain temperature/time guidance, which is substantially implemented by virtue of it being possible to influence the size of the scattering centers therewith. Hence, depending on application wavelength or application wavelength range, it is possible to obtain an optimal scattering effect, and so it is possible to meet requirements, for example in respect of the homogeneity of the emission. The emission characteristic is adjustable in the targeted fashion therewith.

Moreover, further downstream processes are conceivable, in which the intensity profile of the lateral emission of the diffuser main body can be corrected or adapted. In particular, these comprise methods which can, firstly, at least locally modify the properties of the material in its volume and/or on its surfaces, for example the refractive index thereof, and/or the composition thereof, for example as colloidal deposits and/or seed formation and/or crystallization, and can, secondly, facilitate material ablating or applying modifications in virtually any geometric shape and arrangement.

By way of example, these include laser processing methods which, for example by means of short pulse or $CO_2$ lasers, can bring about the introduction of refractive index changes or the production of structures in the volume, for example voids, and/or in the surfaces.

Moreover, printing processes are applicable for applying for producing structures, for example a grid profile structure, on the surface of the diffuser element and/or of the diffuser main body and/or of the jacket, for example by means of printable organic or ceramic colors with corresponding pigments or by means of a glass flow-based color, with appropriate thermal post-treatment where necessary. Photolithographic methods and process steps are also performable, as are used, for example, specifically for volume or surface structuring, for example of photosensitive or photostructurable glasses and glass ceramics.

Likewise possible are possibly selective wet and dry chemical etching of the diffuser main body and/or of the diffuser element at the surfaces thereof, wherein photolithographic processing steps may also be used here. Methods with a mechanical and/or abrasive effect can also be used for structuring, in particular for roughening the surface of the diffuser element and/or of the diffuser main body and/or of the jacket, for example grinding, lapping or sandblasting.

The proposed exemplary processes or methods can also be applied in combination. The diffuser elements producible thus and/or the diffuser main body and/or jackets consequently comprise structures, at least in part or in sections, in the volume thereof and/or on the surfaces thereof.

In a further advantageous embodiment variant, provision can be made for the diffuser main body to have, at least in part and/or in sections, a coating with scattering particles and/or for the diffuser main body to have, at least in part and/or in sections, an additional, further cladding made of a colored glass or colored plastic. Examples of such a coating, which additionally assist a Lambertian emission characteristic and in this case, in particular, reduce an emission directed forwardly in the light input coupling direction, include a coating with boron nitride (BN). Further coatings of this type may consist of titanium oxide, calcium carbonate or zirconium oxide, for example.

By way of example, this additional cladding can be formed from white glass which contains scattering elements in its glass matrix. In the transition region, in the region of the connecting point or in the region of the intermediate medium between diffuser main body and the light guide, a colored glass tube can be provided as additional cladding, the coloration and the intensity of which can be chosen in such a way that the utilized wavelength of the light, in particular, is suppressed or even blocked.

Using this, it is possible to suppress unwanted reflections and hence unwanted emissions. Appropriate claddings made of plastic are, for example, colored silicone or PTFE or FEP tubes. Advantageously, corresponding dipping coatings made of silicone or corresponding plastics or varnishes are also able to be used.

In all of the exemplary embodiments explained above, care has to be taken in view of the smallest possible heating of the component part applied in the body, in particular the components of the component part specified below, that the diffuser element and/or the diffuser main body and/or the jacket have a low absorption at the respective application wavelength. In this case, temperature increases to above 42° C., in particular, should be avoided from a medical point of view. This is even more important if the diffuser is operated with relatively high laser powers, for example for certain types of therapy. Unless this relates to therapies that target the heating of the tissue in particular (e.g., LITT).

The production of the diffuser main body according to the invention with an illumination profile matched to the application, in particular of the homogeneity of the intensity of the radial, spherical emission characteristic desired in the operational state, places significant requirements on the various process steps. Therefore, the production method of the diffuser main body according to the invention is likewise an important further aspect of the present invention.

Therefore, a possible method is specified for producing a diffuser main body, in particular for use on or with an illumination system as explained above, comprising at least one diffuser element with at least one diffuser main body and at least one scattering element, wherein preferably at least one scattering element is arranged in the volume of the diffuser main body, preferably comprising the method steps described below.

In exemplary fashion, a method is specified for producing a diffuser main body made of white glass with scattering particles as scattering centers. A method provides for the white glass to be brought into a rod shaped by means of suitable drawing methods. The diameter of such rods can range between 0.2 mm and 2 mm, or else be larger, and is determined by the desired size of the diffuser main body. Drawing can be implemented directly from a glass melt with a corresponding composition of the components as illustrated above.

Byway of example, the scattering centers in the white glass rod can be formed by scattering particles or by inhomogeneous regions. The diameter of the scattering centers in such a rod can preferably range from 10 nm to 2000 nm, particularly preferably from 100 nm to 1200 nm.

If scattering particles that should be embedded in the volume of the material of the rod are used as scattering centers, these can be supplied particularly expediently to the melt. These scattering particles can comprise $SiO_2$ and/or SiN and/or BaO and/or MgO and/or ZnO and/or $Al_2O_3$ and/or AlN and/or $TiO_2$ and/or $ZrO_2$ and/or $Y_2O_3$ and/or only the metals of these oxides and/or BN and/or $B_2O_3$ and/or Ru and/or Os and/or Rh and/or Ir and/or Ag and/or Au and/or Pd and/or Pt and/or diamond-like carbon and/or glass ceramic particles.

The concentration of the scattering particles in the melt likewise depends on the concentration desired for the diffuser main body and can preferably be between 10 ppm and 1000 ppm, particularly preferably between 20 ppm and 100 ppm. After addition of the scattering particles, the glass melt is advantageously homogenized, for example by means of suitable stirrers, in order to obtain the desired uniform distribution, which can be determined on the basis of samples obtained from the melt.

By contrast, if inhomogeneous regions of the glass should be used as scattering centers, the concentration of the inhomogeneous region in the glass rod is preferably between 1% and 80%, particularly preferably between 10% and 50% (in percent by volume). The inhomogeneous regions in the glass rod are preferably formed by phase separation and/or demixing of the glass components of the glass, in which they are embedded.

That is to say, e.g., drop-shaped demixing zones or demixing regions with a second refractive index that deviate from the first refractive index can form in the glass, said glass having the first refractive index and said demixing zones or demixing regions being formed from some of the glass components of the base glass with the first refractive index. Consequently, these demixing regions with the refractive index have a different composition of the surrounding glass and can consequently also have other physical properties, for example precisely a different refractive index and/or different coefficient of expansion.

Preferably, the glass in which the inhomogeneous regions are embedded as scattering centers consists of an As—Pb-containing silicate glass. In this case, the inhomogeneous regions can have an elevated Pb and/or As content in relation to the surrounding glass matrix. Alternatively, the glass in which the inhomogeneous regions are embedded as scattering centers preferably consists of a fluorine-containing silicate glass. Then, the inhomogeneous regions can have an elevated fluorine content in relation to the surroundings glass matrix of the rod.

By way of a drawing process, it is possible to produce a glass rod with the desired distribution and concentration of the scattering centers. The latter can subsequently be cut to a suitable length and, by applying a subsequent thermal process to the sections produced in this way, the desired external geometry can be produced by forming.

The method described here for producing the diffuser main body can also be used, in principle, for other glass types, for instance for borosilicate glass systems.

The diffuser main body obtain in this fashion can then be securely connected to the light guide by means of adhesive bonding or splicing.

A dipping process can be provided prior to or after the connection of the diffuser main body to the light guide, in order to produce a jacket which preferably completely surrounds the diffuser main body. Since it is advantageous for the durability of the connecting point if the latter is also protected by a jacket, dipping is advantageously only implemented after the diffuser main body was connected to the light guide. In this way, it is possible for the connecting zone between diffuser main body and light guide, for example the splicing region, to also be enclosed.

In this case, as explained above, the jacket can comprise a layer that is transparent or translucent to light emitted laterally from the diffuser element and consists of liquid silicone, thermoplastic polymer, hot melt adhesive, 2-component adhesive or sol-gel glass, a shrink tubing or else additionally applied transparent or translucent attachment elements, which surround the diffuser main body and/or the transition point at least in part or in sections, or else in full, between diffuser main body and light guide.

Byway of example, in the case of an LAS glass ceramic, an originally clear transparent high quartz mixed crystal phase can be brought into an opaque keatite phase, which can represent the scattering centers, by crystal conversion byway of the temperature control during the ceramicization.

Additionally, a method is also specified for at least partial or sectional structuring, in particular for adapting the intensity profile of the emission of the diffusion main body, wherein the diffuser main body and/or the connecting zone to the light guide is surrounded at least in part or in sections, or else in full, by a transparent or translucent jacket and forms the diffuser element.

This jacket is preferably formed from flexible tube, the tube preferably containing scattering centers which at least locally modify its properties and/or composition in the volume and/or at the surfaces and/or which form material ablating or applying structures in virtually any geometric form and arrangement therein and/or thereon, comprising methods of the laser processing, in particular by means of short pulse or $CO_2$ lasers which preferably introduce refractive index and/or composition changes or produce structures in the volume and/or on the surfaces, printing processes for applying or producing a grid profile structure in particular by means of printable organic or ceramic colors with corresponding pigments or by means of glass flow-based colors, methods of wet chemical or dry chemical etching, photolithographic methods, abrasive, mechanical processing methods or a combination of these methods.

A preferred use of the illumination system as described above and its various embodiment variants is provided for the use for photodynamic therapy (PDT), for example for tumor therapy, e.g., in the brain, in the long, in the respiratory tract, in the bladder or in the uterus. Likewise conceivable is the use for endovenous laser therapy (EVLT), for example for treating varicose veins, for a laser induced interstitial thermal therapy (LITT) or for applications in the field of dentistry, for a bladder or prostate treatment, for a light induced treatment of inflammations in the neck/pharynx (mucositis), in ophthalmology and in dermatology, as described at the outset. In the field of dentistry, applications for wound treatment or periodontal disease treatment, in particular, should be mentioned here, wherein gingival sulci can be illuminated correspondingly efficiently by means of such diffusers. In ophthalmology, this allows the provision of probes which can be pieced into the eyeball in the case of interventions in the region of the retina such that it is possible to uniformly illuminate large regions of the retina. Moreover, there are applications in brain research, in which individual brain regions can be stimulated by means of light and hence pathological symptoms can be treated therewith.

A further use of the illumination system as described in its various embodiment variants above provides for the use for photodynamic therapy (PDT) or photoimmunotherapy (PIT) for tumor therapy, at least one light guide with the diffuser element takes up light emitted from other diffuser elements and transmits said light via the light guide to a detector for spectroscopic analysis. In the process, light receiving diffuser light guides are also applied to the patient in addition to the various light emitting diffuser light guides, wherein a response to the PDT treatment can be deduced on the basis of the spectral differences between input coupled and received light (in this respect, see Finlay et al., Proc. SPIE Int. Soc. Opt. Eng. 2014, Jun. 14; 5315: page 132-142). PIT treatments are described, inter alia, in "Study of RM-1929 and Photoimmunotherapy in Patients With Recurrent Head and Neck Cancer", US National Library Medicine.

In view of dosimetry measurements in the PDT or PIT treatment, the above-described diffuser light elements can also be used to detect the light scattered back from the tissue. Using this, it is firstly possible to carry out spectroscopic examinations if, in particular, the back-scattered light is analyzed at wavelengths that differ from those of the radiated in light. Using this, it is possible to detect the extent to which the photosensitizer has completely reacted, for example. Secondly, intensity measurements can also provide information in respect of the extent to which the irradiation of the tumor-afflicted tissue was sufficient or has not been overexposed.

Moreover, industrial applications also advantageous, for example for inspecting hard to access locations, for example on or in a machine, where homogeneous illumination is particularly important, or else spectroscopic applications or applications in biochemistry, in which biochemical in vitro reactions are stimulated by light.

BRIEF DESCRIPTION OF THE FIGURES

The invention will be explained in more detail below on the basis of an exemplary embodiment illustrated in the figures. In detail.

DETAILED DESCRIPTION

In the following description of the detailed embodiments, the same reference signs in the attached figures in each case referred to the same constituent parts or constituent parts with the same effect.

The following definitions are provided for a better understanding.

Within the meaning of the present disclosure, the term illumination system comprises illumination apparatuses and, in particular, illumination apparatuses which are suitable for use of in medical engineering purposes and, in particular, disinfectable and/or sterilizable at least in sections, provided that these come into contact with living tissue.

Figure 1:
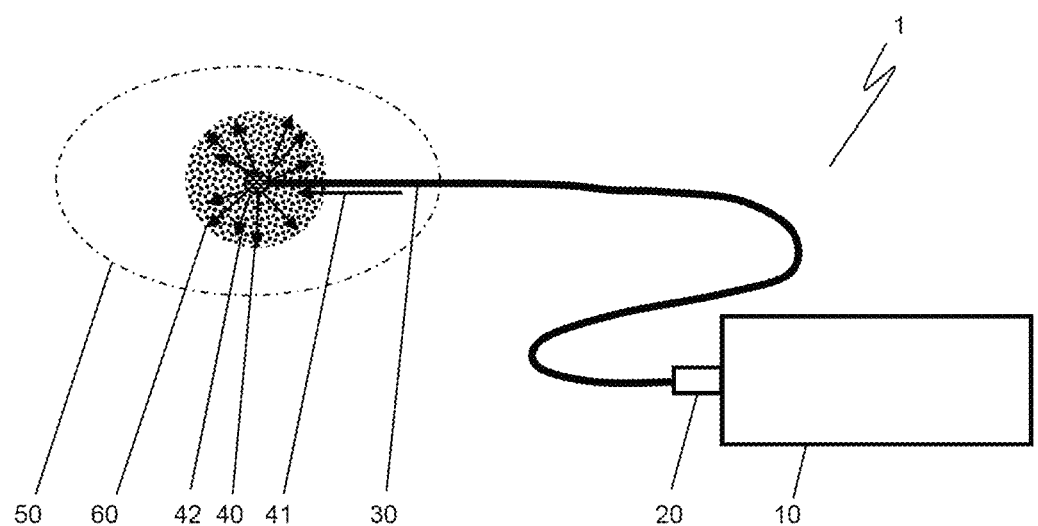
FIG. 1 schematically shows an illumination system with a light guide and a diffuser element in a PDT application.

The statement "for a medical therapeutic and/or diagnostic system" also comprises the use or application of the illumination system as disclosed herein itself as a medical therapeutic and/or diagnostic system FIG. 1 schematically shows the setup of an illumination system 1 according to the one preferred embodiment of the invention. A medical PDT application is illustrated in exemplary fashion in this case.

In the shown example, the illumination system 1 comprises a laser light source 10, which emits light in a certain spectral range when in operation. For PDT applications, as described the outset, use is made of lasers which emit at a wavelength matched to a biochemically modified dye (photosensitizer) administered previously, usually in the visible range, for example in the green spectral range at 532 nm or in the red spectral range at 690 nm, for example.

A light guide 30 is connected at its proximal end to the laser light source 10 using a connector 20. Here, the proximal end refers to the end of the light guide 30 where light is coupled in. At the distal end, the light guide 30 comprises a diffuser element 40, which is introduced, either directly or possibly via cannulas not illustrated here, into a tumor tissue 60 that has formed within healthy tissue 50. Here, the distal end refers to the other end of the light guide 30 which, as a rule, is arranged at a distance from the proximal end of the light guide 30 and from which light, in particular, emerges.

In this case, the laser radiation reaches into the diffuser element 40 by way of light input coupling 41 at the diffuser element 40 and said laser radiation is scattered multiple times in the diffuser element 40 and emitted via the surface thereof, substantially in radial spherical fashion. In the example illustrated, the light output coupling is shown on the basis of purely exemplary rays 42. Here, it comes down to an emission that is as homogeneous as possible into a sphere surrounding the diffuser element 40. In particular, intensity peaks should be avoided. As a result of the photoinduced biochemical reaction, as described at the outset, there ideally is necrosis of the tumor tissue 60 following the treatment.

As a rule, quartz fibers are used as light guides 30, wherein the connectors 20 are embodied, as a rule, as coaxial plug-in connectors, so-called SMA connectors or FC connectors, in which the fibers are adhesively bonded into the connector 20. Connectors 20 with nickel silver sleeves can also be advantageous in respect of the thermal resilience; here, the light guide 30 is introduced, crimped, into the nickel silver sleeve in interlocking fashion byway of a plastic deformation. Moreover, in the case of greater laser powers, use can also be made of connectors 20 in which the fiber end of the light guide 30 is protected by conical prism; this may be advantageous in the case of misalignments.

Figures 2A, 2B, 2C:
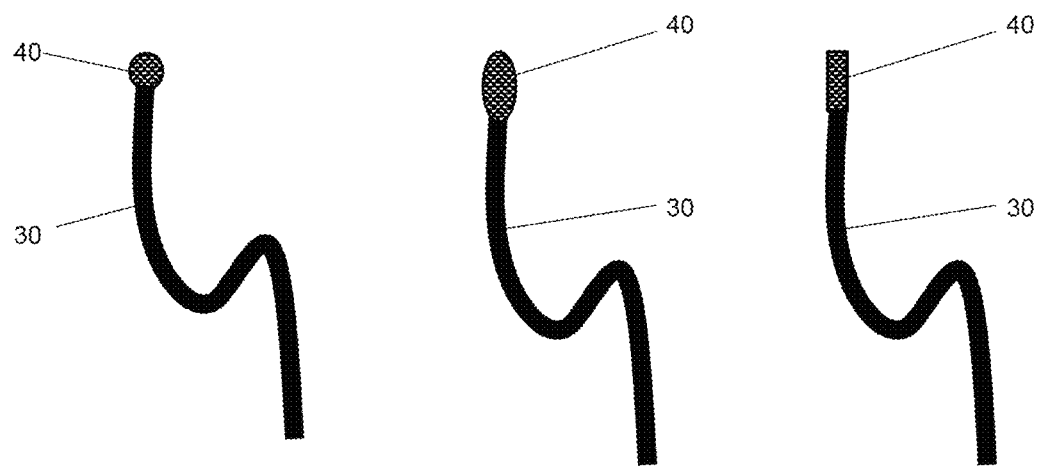
FIG. 2a to 2c show schematic illustrations of different geometric manifestations of the diffuser element.

FIGS. 2a to 2c show, in exemplary fashion and in a schematic illustration, various preferred geometric manifestations for a diffuser element 40 emitting substantially spherically in this way. FIG. 2a shows a diffuser element 40 which has a substantially spherical geometry. FIG. 2b shows an example of a diffuser element embodied as an ellipsoid. FIG. 2c shows an example in which the diffuser element 40 is embodied as a short cylindrical section. In this respect, it should be noted it other geometries, e.g., drop-shaped or oval geometries, or geometries that can be represented as a superimposition or combination of the aforementioned basic geometric shapes, are also included here. Dome-shaped geometries are also conceivable. The rather short overall length of the diffuser element 40 in relation to the external diameter of the light guide 30 is characteristic in this case. Usually, the latter is between 300 µm and 800 µm for the quartz fibers used, and so typical lengths of the diffuser element 40 according to the invention accordingly range between 200 µm and at most 10 mm.

Figure 3:
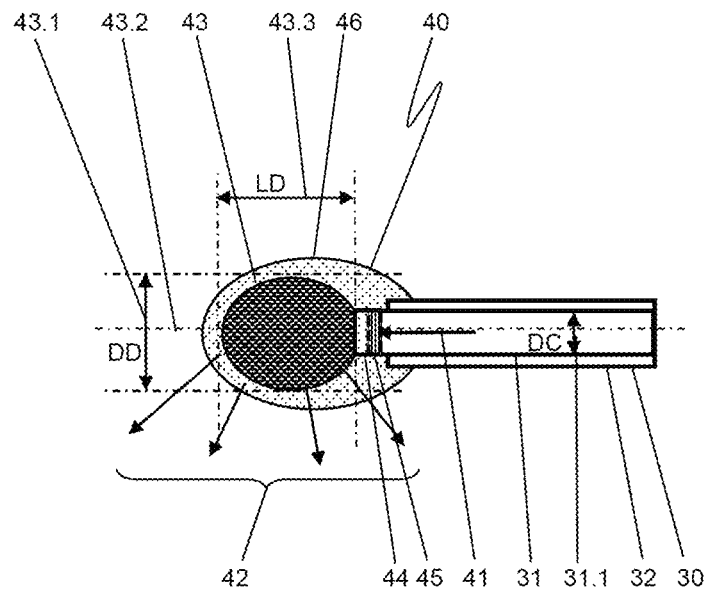
FIG. 3 shows a detailed schematic illustration of a cross section through a diffuser element with a light guide.

FIG. 3 shows a detailed schematic illustration of a cross section through a diffuser element 40 with a light guide 30.

Diffuser main body 43 and light guide 30 are fastened within the connecting zone 44, for example by way of a splicing or adhesive bonding process with a refractive index-matched highly transparent adhesive. During splicing, the light guide 30 and the diffuser main body 43 are partially melted or melted by means of a corona discharge and/or by means of the laser, usually a $CO_2$ laser, and are brought together. Depending on the material used for the diffuser main body 43 and the light guide 30, it may be necessary to use an intermediate medium 45 for the purposes of matching their coefficients of the thermal expansion. In the case of glass/quartz fusion, this may be the soldering or transition glass or an optical adhesive or cement.

In the above-described applications, the light guide 30 usually consists of quartz glass with a core 31 with the refractive index $n_1$ and a core diameter DC 31.1 of usually between 200 and 800 µm and a cladding 32 with the refractive index $n_2$, where $n_1 > n_2$ applies.

Usually, such a fiber also has an outer polymer layer referred to as a buffer, consisting of polyamide or polyimide, for example. The numerical aperture NA usually obtainable there with is approximately 0.22. Light input coupling 41 is implemented by way of an input coupling face, which is formed by a connecting zone 44 of the diffuser main body 43.

As illustrated in exemplary fashion, the diffuser main body 43 can have an ellipsoid cross section. As illustrated above (cf. FIGS. 2a to 2c), different shapes can also be applicable to the diffuser main body 43. In this case, the diameter DD 43.1 of the diffuser main body 4, with this meaning an extent in a direction perpendicular to the direction of the light input coupling, i.e., perpendicular to the longitudinal direction of the light guide in the region of the input coupling, and the diffuser length LD 43.3 along its longitudinal axis 43.2, provided the latter has, e.g., a rather oval or elliptic manifestation, i.e., is parallel to the direction of the light input coupling or in a direction parallel to the longitudinal direction of the light guide in the region of the input coupling, are geometrically characteristic.

According to the invention and as described above, the diffuser main body 43 consists of an inorganic material, in particular a glass, a glass ceramic or a glass-like substance, in which, on account of its composition, finely distributed scattering centers with a certain size distribution are able to be formed in a targeted manner. The above-described material approaches are particularly suitable to this end.

For protection purposes, the diffuser main body 43 is provided with a jacket 46 that completely surrounds the diffuser main body 43, wherein it may be advantageous if the connecting zone 44 between diffuser main body 43 and light guide 30 is additionally also surrounded. Usually, the light guide 30 does not have a buffer layer in this region (illustrated in FIG. 3 without cladding 32), and so this zone can be protected by such a jacket 46, with this otherwise having to be implemented by way of a so-called recoating process for mechanical protection.

In this case, the jacket 46 can consist of a layer that is transparent or translucent to light emitted laterally from the diffuser element and consists of liquid silicone, thermoplastic polymer, hot melt adhesive, 2-component adhesive or sol-gel glass, of a varnish layer, of a shrink tubing or of additionally applied transparent or translucent attachment elements, which surround the diffuser main body 43 and the transition point between diffuser main body 43 and light guide 30.

An inclusion with a glass that melts at comparatively low temperatures is also conceivable, wherein care has to be taken in this case, however, that there is not an inexpedient intervention in the emission characteristic of the diffuser element when applying the glass that melts at low temperatures at an elevated temperature.

In an advantageous configuration, the diameter DD 43.1 of the diffuser main body 43 is designed to be greater than the core diameter 31.1 or the fiber bundle diameter 31.1 of the light guide 30 such that the light is coupled into the diffuser main body 43 in optimal fashion. Secondly, this can simplify assembly and adjustment of light guide 30 and diffuser main body 43 and/or compensate for assembly tolerances. What can moreover be achieved is that it is possible to still obtain a certain amount of light propagation directed backward, i.e., in a direction of the light introduction by the light guide.

Figure 4:
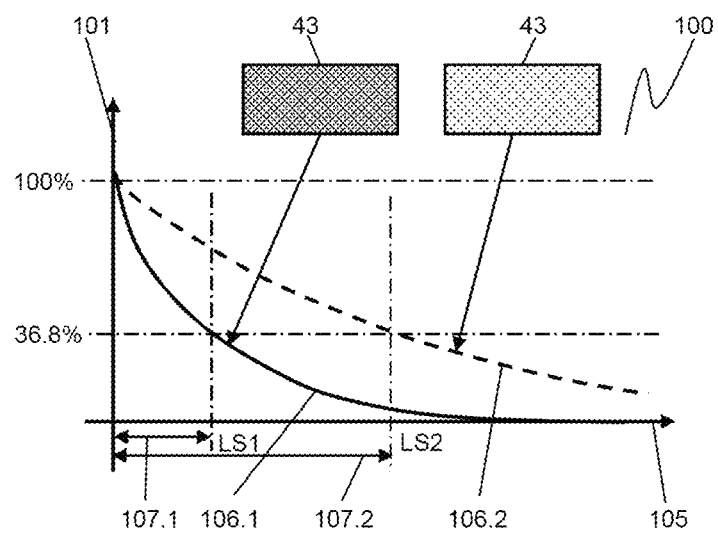
FIG. 4 shows a graph of angle-dependent intensity profiles.

In a graph 100, FIG. 4 describes an intensity profile for two diffuser main bodies 43, which are embodied as a rod-shaped material for the purposes of empirically determining a specific scattering length 107.1, 107.2. Shown by way of a first intensity profile 106.1 and a second intensity profile 106.2 are the intensities 101 measured perpendicular to the rod axis as a function of the distance from the connecting zone $I_{(x)}$ 44 or light input coupling point, which is located on the left-hand side in the graph 100, wherein the intensity values 106.1, 106.2 are normalized to 100% directly at light input coupling point. In both cases, the intensity 101 reduces approximately according to an exponential function as per the following relationship, provided the scattering effect is constant over the length of the rods:

$$I_{(X)}=I_0*\exp(-X/LS) \quad (1)$$

where $I_0$ represents the initial intensity of the light input coupling point and $I_{(x)}$ represents the measured intensities 101 as a function of the distance from the connecting zone $I_{(x)}$44.

In this case, the specific scattering length LS1, LS2 107.1, 107.2 is defined as the distance from the light input coupling point at which the light intensity is dropped to the value of 1/e or to 36.8%. Shown in exemplary fashion is the diffuser main body 43 with comparatively intensive light scattering (left-hand diffuser main body 43), which is expressed in a steep intensity profile 106.1 and, corresponding therewith, a comparatively short scattering length LS1 107.1. The diffuser main body 43 illustrated on the right-hand side shows a less intense scattering effect, which is expressed in a rather flat or intensity profile 106.2 and, corresponding therewith, a comparatively longer scattering length LS2 107.2. According to the invention, the material of the diffuser main bodies 43 can be set in respect of its scattering properties by way of targeted temperature/time processes, as already described above, and can be characterized quantitatively using such a measurement.

In order to obtain an ideal, radially uniform intensity distribution, there are requirements in respect of the geometry, in particular in respect of the diameter of the diffuser DD 43.1 and the diffuser length DL 43.3 based on the scattering properties of the diffuser main body, which, at least to a first approximation, can be described empirically by the specific scattering length LS1, LS2 107.1, 107.2. In this case, the core diameter DC 31.1 of the light guide 30 or fiber bundle diameter also plays a certain role. In the process, the following geometric relationships were found to be expedient:

Furthermore, the radial, spherical emission characteristic is promoted by an extent of the diffuser main body in which the greatest extent LD of the diffuser main body in a first direction is no more than 10 times, preferably 5 times and particularly preferably 2.5 times the extent of the diffuser main body in a second direction DD perpendicular to this first direction, preferably no more than 2 times and particular preferably no more than at 1.5 times.

In a particularly preferred embodiment, the extent of the diffuser main body in a first direction equals the extent of the diffuser main body in a second direction perpendicular to this first direction, as a result of which a spherical embodiment is provided.

For the quartz fibers used, the external diameters of the light guides usually range between 200 μm and 800 μm, and so typical extents of the diffuser element can range between 300 μm and 3 mm in a preferred embodiment of the invention. The maximum extent of the diffuser main body LD in one direction ranges between 200 m and 10 mm, preferably between 250 μm and 4 mm, in particular preferably between 300 μm and 3 mm.

Preferably, the following furthermore applies to the core diameter DC:

$$DD \leq DC \quad (2)$$

where, typically, D ranges between 200 m an 00 μm, preferably between 300 μm and 400 μm. The ratio of the core diameter DC 31.1 or fiber bundle diameter of the light guide 30 to the diameter of the diffuser main body OD 43.1 therefore is advantageously ≤1.0, preferably between 1.0 and 0.8. Depending on the desired emission characteristic, a ratio of 0.8 may also be provided.

For the diameter of the diffuser main body 43 embodied as a ball or for the diffuser length LD 43.3 of a rather elongate diffuser main body 43, the following geometric conditions arise, wherein an expedient value for LS was found to be where LS approximately corresponds to the length of the diffuser main body LD 43.3:

$$LD \leq LS \text{ and} \quad (3)$$

$$LD \leq 3*DC, \text{ preferably } LD \leq 2*DC \quad (4)$$

Figure 5:
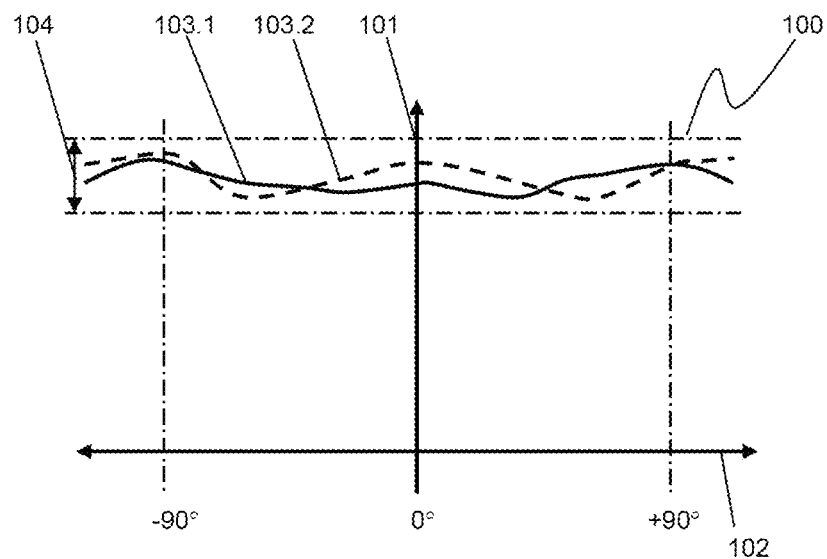
FIG. 5 shows a further of an intensity profile and a respective specific scattering length for two different scattering diffuser main bodies, FIG. 6 schematically shows a diffuser element embodied as a balloon catheter.

The result of such a geometric selection yields the graph 100 shown in FIG. 5, in which the intensity 101 is plotted as a function of an observation angle 102 at an equidistant distance around the diffuser element 30. A first intensity profile 103.1 shows an intensity measurement in a horizontal plane around the diffuser element 40. A second intensity profile 103.2 shows the result of an intensity measurement in a perpendicular plane, which is orthogonal to the first horizontal plane, around the diffuser element 40. It is evident that both intensity curves 103.1 and 103.2 lie in a tight intensity tolerance band 104. Typical obtainable values therefore lie under ±20%, preferably under ±15% and particularly preferably under ±10%.

If the aforementioned geometric relationships have not been chosen optimally, there would be a significant excess in the intensity curve 103.1, 103.2 in the region around 0°, i.e., as seen in the forward direction of light propagation, for example if the specific scattering length LS is significantly greater than the diffuser length LD 43.3 or the diameter of the diffuser main body 43 in the case of a rather spherical geometry. By contrast, a significant indent could be identified in the intensity profile 103.1, 103.2 at approximately 0° if the specific scattering length LS is significantly less than the diffuser length LD 43.3 or the diameter of the diffuser main body 43 in the case of a rather spherical geometry.

Figure 6:
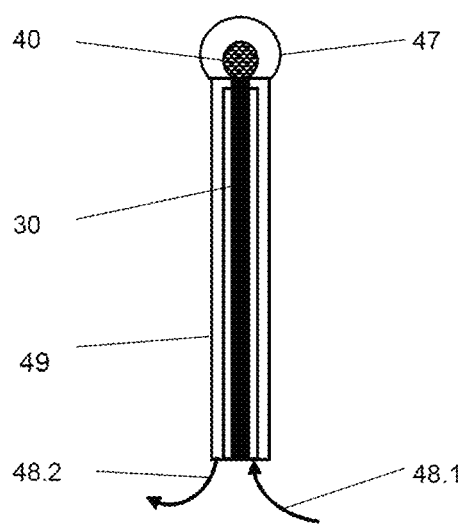

As a further exemplary embodiment, FIG. 6 shows a diffuser that is integrated within a balloon catheter. Illustrated schematically is the diffuser element 40, as described above, which has been spliced to a light guide 30 which is embodied as a quartz fiber and located in a balloon 47 that can be inflated during the treatment. Particularly in the case of relatively high laser talents, provision can furthermore be made for a cooling liquid, e.g., a 0.9 percent saline or water, to be able to circulate around or on the light guide via additional supply and discharge channels (see liquid supply and discharge 48.1, 48.2), helping to substantially reduce the heat input into the tissue.

Figures 7A, 7B, 7C:
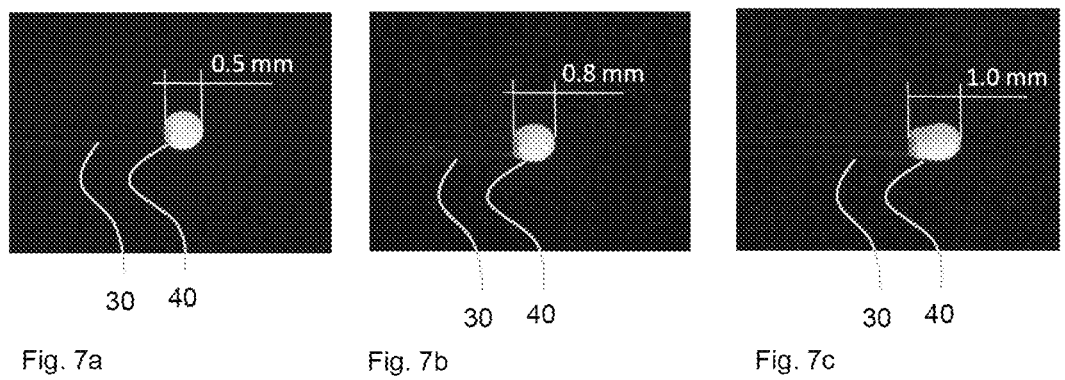
FIG. 7a to 7c show diffuser elements with different lengths and FIG. 8 shows a further graph of angle-dependent intensity profiles for the diffuser elements shown in FIGS. 7a to 7c, including a schematic illustration of the measurement principle.

FIGS. 7a to 7c show diffuser elements 40 with different geometries. FIG. 7a shows the diffuser element 40, the diffuser length 43.3 LD of which is approximately 0.5 mm following a rounding process. FIG. 7b shows a diffuser element 40, the diffuser length 43.3 LD of which is approximately 0.8 mm following the rounding process, and FIG. 7c shows a diffuser element 40, the diffuser length 43.3 LD of which is approximately 1.0 mm following the rounding process.

Figure 8:
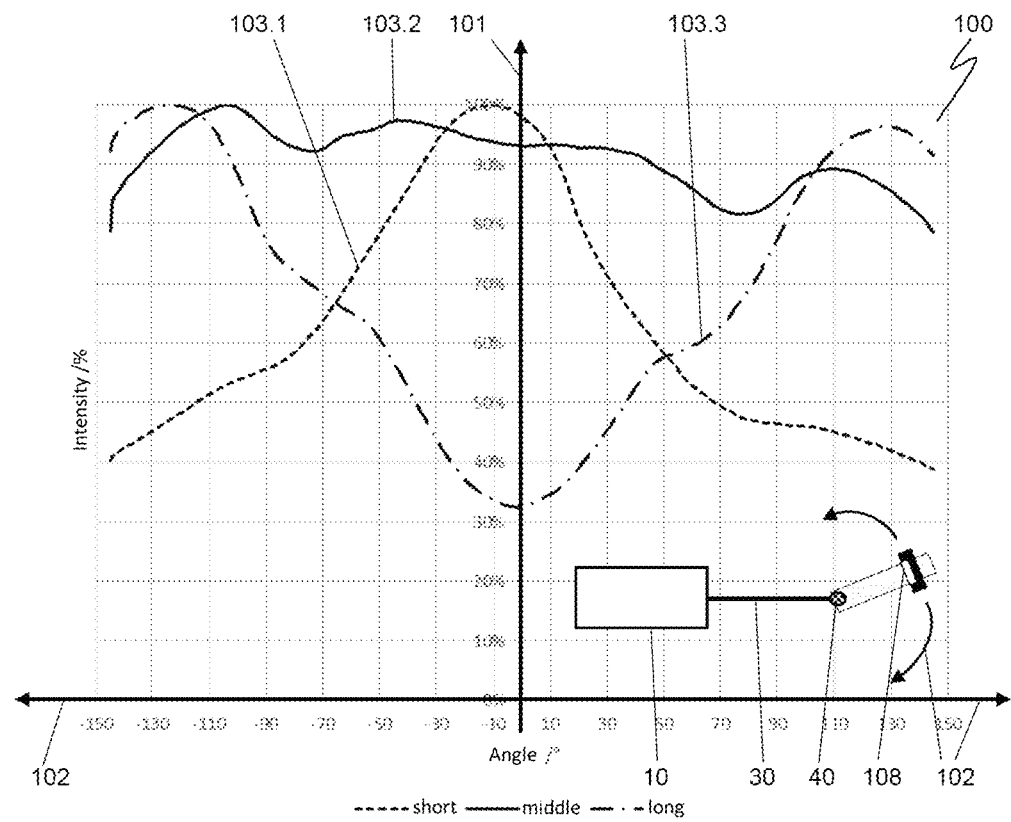

In a further graph 100 in FIG. 8, corresponding measured intensity profiles 103.1, 103.2, 103.3 are illustrated as azimuth scans for the diffuser elements 40 shown in FIGS. 7a to 7c, with the respective intensity 101 being plotted as a function of the observation angle 102. The schematic illustration in FIG. 8 shows the measurement principle of the goniometer measurement. The diffuser element 40 is irradiated by means of the laser light source 10 via a quartz fiber (light guide 30) spliced onset a diffuser element, and emits the light in radial/spherical fashion. In the process, a detector 108 is pivoted around the diffuser main body 40 at a constant distance, approximately 35 mm in this case, and the intensity 101 is measured as a function of the observation angle 102 in the process. In the FIG. 8, the intensity profiles 103.1, 103.2, 103.3 are normalized in this case to the highest measured intensity 101 (=100%). The measurements of be carried out using the following settings and the following hardware:

Goniometer measurement range: −145° to +1450
Distance between detector 198 and diffuser element 40: 35 mm
GIGAHERTZ OPTIK Optometer P-2000
Sensitivity function: radiometric 400 nm to 1000 nm
Typical sensitivity: 10 nA/(W/m$^2$)
Detector aperture diameter (diffusion panel): 11 mm
Measurement opening cosine field of view
Laser light source 10: 4 mW @ 655 nm The 1st intensity profile 103.1 shows the emission characteristic for the diffuser element 40 illustrated in FIG. 7a, with a typical diffuser length LD 43.3 of 0.5 mm. It is evident here that this diffuser element 40 is comparatively too short in comparison with its characteristic of scattering length LS. This is evident from the pronounced intensity peak in the region around 0°. The 2nd intensity profile 103.2 shows the emission characteristic for the diffuser element 40 illustrated in FIG. 7b, with a typical diffuser length LD 43.3 of 0.8 mm. It is evident here that this diffuser element 40 is matched in respect of the diffuser length LD 43.3 in comparison with its scattering length LS, and hence also results in an approximately uniform intensity 101. The 3rd intensity profile 103.3 shows the emission characteristic for the diffuser element 40 illustrated in FIG. 7c, with a typical diffuser length LD 43.3 of 1.0 mm. It is evident here that this diffuser element 40 is comparatively too long in comparison with its characteristic of scattering length LS. The consequence is a significant drop in intensity in the region around 0°.

Figure 9:
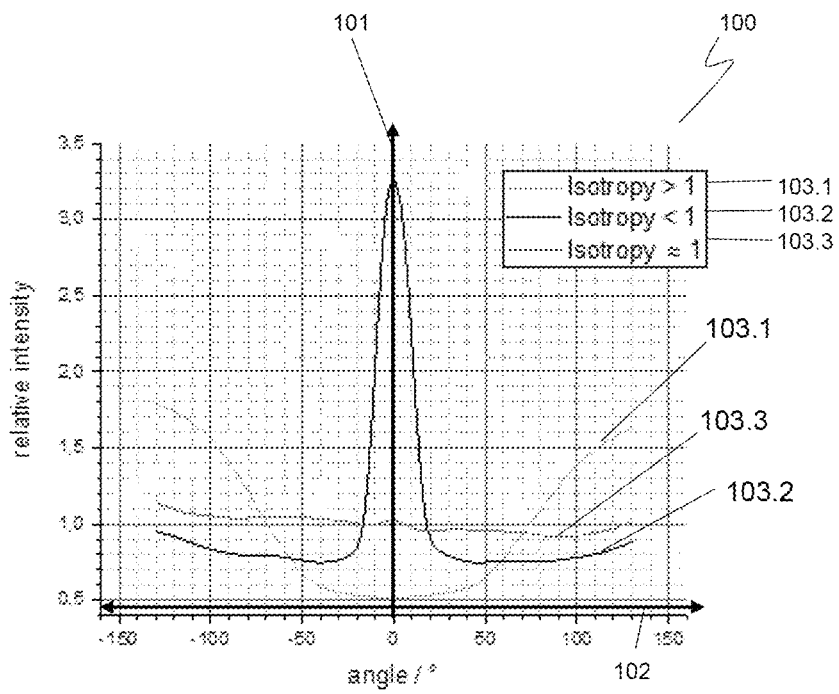
FIG. 9 shows a further graph for a spherical diffuser, which is embodied as a ball and in which the diffuser material was subjected to a different thermal pretreatment.

FIG. 9 shows a further graph 100 of a spherical diffuser embodied as a ball, in which the diffuser material was subjected to a different thermal pretreatment. Plotted are the intensity profiles 103.1, 103.2, 103.3 of a relative intensity 101 as a function of the observation angle 102.

The 1st intensity profile 103.1 shows, in exemplary fashion, a more laterally emitting characteristic, which corresponds to an isotropy >1. In this case, the scattering behavior has been set to be so strong that the radiation coupled into the diffuser is scattered to the side at already a relatively early stage and only a comparatively small proportion is let through in the forward direction.

By contrast, the 2nd intensity profile 103.2 shows a profile in which only a small proportion is scattered to the side and, instead, the predominant part of the input coupled light power is transmitted in the forward direction, corresponding to an isotropy <1.

The 3rd intensity profile 103.3 shows an example for an approximately uniform emission in each spatial direction, corresponding to an isotropy of approximately 1. The intensity profiles 103.1 to 103.3 can be influenced by targeted and monitored temperature/time process management for the above-described materials.

The example shown relates to the CoralPor™ glass material, as described above. In this case, the laser wavelength is 655 nm.

Figure 10:
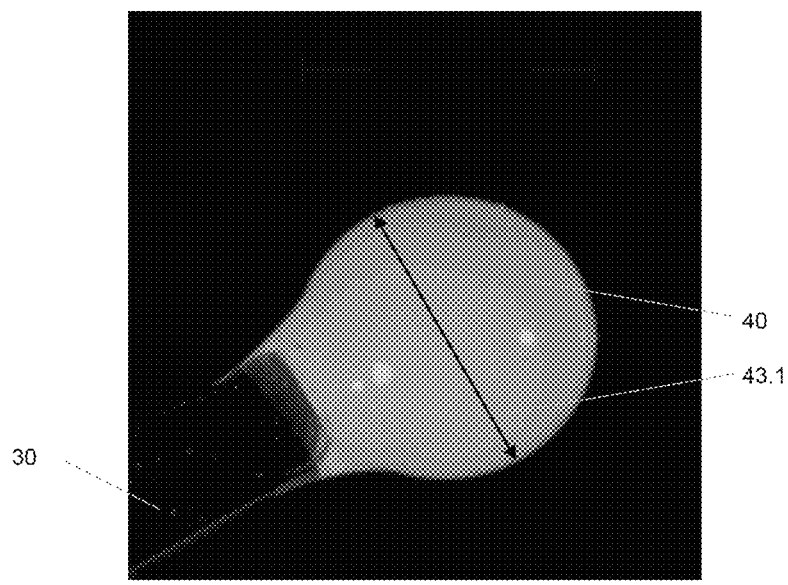
FIG. 10 shows a diffuser embodied substantially as a ball.

FIG. 10 shows the diffuser in a microscope image. In this case, the diffuser element 40 is substantially embodied as a ball or in spherical fashion and has a diffuser diameter 43.1 of approximately 1 mm. The light guide 30 has the fiber core diameter of approximately 400 μm, corresponding in the example shown to a core diameter of the light guide to diameter of the diffuser main body 43 ratio of approximately 0.4.

Figure 11:
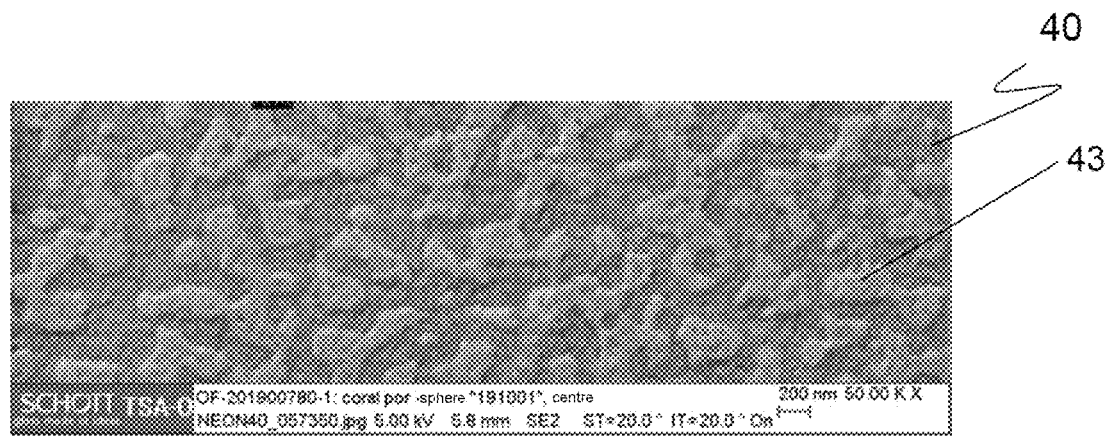
FIG. 11 shows and SEM recording of the cross section of the diffuser embodied as a ball in the center of the ball.
Figure 12:
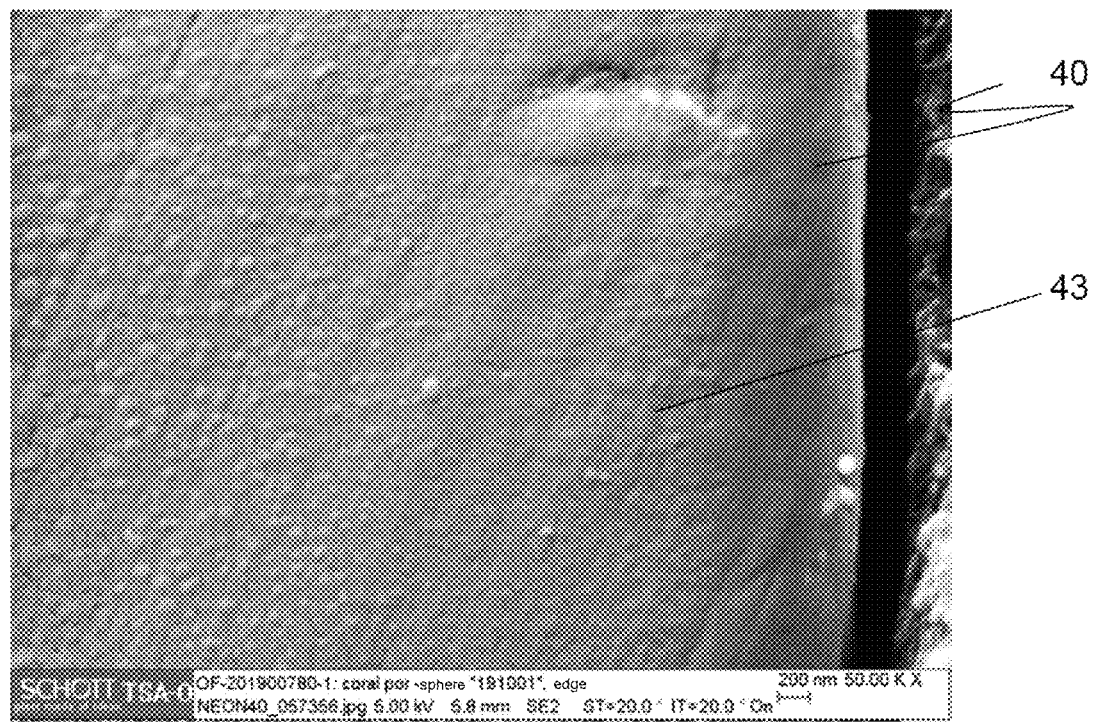
FIG. 12 shows a further SEM recording of the cross section of the diffuser in a surface-near zone.

FIG. 11 shows the ball center of the diffuser main body 43 of the diffuser element 40 from FIG. 10 in an SEM recording as sectional image. In this case, the polished cross-section was etched with XeF2 gas before the SEM recordings in order to identify the two different phases of the glass in the polished cross-section. In the center of the ball there is a penetration structure with structure extents of approximately 200 nm; from a plurality of micrometers below the ball surface, this structure becomes looser towards the surface, as can be identified in FIG. 12, and forms a rather amorphous flat surface.

For further mechanical protection and/or for homogenization of the emission characteristic, provision can be made of a further cladding 49 made of transparent and/or translucent, colored or colorless material (silicone, glass or quartz glass), which surrounds the diffuser main body and/or the jacket at least in part or in sections, or else in full. In particular, additional homogenization can be obtained using a translucent material and/or a material containing scattering centers. Byway of example, suitable are corresponding bodies or tubes made of silicone, Teflon or else a polyether block amide block copolymer, which is known under the trade name PEBAX®, for example. Thin-walled shrink tubing, which is, e.g., made of PET, which can have a single ply or multi-ply embodiment, and which is applied at least in sections has proven their worth as a cladding 49.

Between the diffuser main body 43 and the cladding 49 made of, e.g., glass or plastic, provision can be made for a further layer to be introduced between cladding 49 and diffuser main body 43 for the purposes of suppressing possible surface irregularities, such as, e.g., dirt, roughness or the like on the diffuser main body 43, which have an inexpedient influence on the emission behavior. Here, care should be taken to have, firstly, a refractive index matched to the glass system, a high transparency and a sufficiently high viscosity in view of good applicability. Byway of example, glycerol or silicones (oils adhesive) were found to be suitable for the further layer.

Therefore, one embodiment with scattering elements 43.6 made of white glass provides for the scattering centers to be formed by the scattering particles, with the concentrations of the scattering particles in the scattering region ranging from 10 ppm to 1000 ppm and preferably from 20 ppm to 100 ppm.

The efficiency of the output coupling from the scattering region, and hence from the volume of the white glass of the scattering rods or of the white glass tube, in addition to the scattering property of the scattering particles as intrinsic parameter also depends on the concentration of the scattering particles in the scattering region.

In this case, the specification of concentration in ppm refers to the proportion of the scattering particles in relation to the proportions by mass of the constituent parts of white glass in which the scattering particles are embedded.

If inhomogeneous regions of the white glass serve as scattering centers, this yields an alternative embodiment in which the inhomogeneous regions are preferably formed by phase separation and/or demixing of the glass components of the glass in which they are embedded.

The scattering centers formed by inhomogeneous regions preferably have a diameter or maximum extent of 10 nm to 1000 nm, particularly preferably of 100 nm to 800 nm. These scattering centers particularly preferably are spherical.

The white glass in which the inhomogeneous regions are embedded as scattering centers can preferably consist of an As- and Pb-containing silicate glass. In this case, the scattering centers have a content of Pb and/or As that is elevated in relation to the surrounding glass matrix.

Alternatively, the glass or white glass in which the inhomogeneous regions are embedded as scattering centers can consist of a fluorine-containing silicate glass. Then, the scattering centers preferably have an elevated fluorine content in relation to the surroundings glass matrix.

Thus, depending on the utilized material and the material properties of the scattering elements 43.6 and the matrix 43.4 surrounding the latter, what can be achieved by a gradient heat treatment is that the scattering effect can be varied, for example continuously, byway of applying different temperatures along the direction of greatest extent of the diffuser. As a result of this, it is possible to initially set a rather low scattering effect, for example for a volume region arranged directly at the input coupling face, and to set a rather higher scattering effect for an opposing volume region of the diffuser main body 43.

Using this, it is possible to obtain diffuser main bodies which have scattering elements with scattering centers with a scattering center density per volume unit, with the scattering center density being different in different volume regions. Consequently, a possible drop an intensity along a direction parallel to the direction of input coupling of the light can be at least partly compensated for.

In a physical sense, the intensity or intensity distribution disclosed presently and mentioned in the claims also corresponds to the luminance, which is also referred to as relative luminance or brightness, provided, like in the present case, measurements are carried out using an optical system that captures a fixed solid angle.

LIST OF REFERENCE SIGNS:

| | |
|---|---|
| 1 | Illumination system |
| 10 | Laser light source |
| 20 | Connector |
| 30 | Light guide |
| 31 | Core |

-continued

LIST OF REFERENCE SIGNS:

| | |
|---|---|
| 31.1 | Core diameter DC or fiber bundle diameter |
| 32 | Cladding |
| 40 | Diffuser element |
| 41 | Light input coupling |
| 42 | Light output coupling |
| 43 | Diffuser main body |
| 43.1 | Diameter DD |
| 43.2 | Longitudinal axis |
| 43.3 | Diffuser length LD |
| 44 | Connecting zone |
| 45 | Intermediate medium |
| 46 | Jacket |
| 47 | Balloon |
| 48.1 | Liquid supply |
| 48.2 | Liquid discharge |
| 49 | Cladding |
| 50 | Tissue |
| 60 | Tumor tissue |
| 100 | Graph |
| 101 | Intensity |
| 102 | Observation angle |
| 103.1 | 1st intensity profile |
| 103.2 | 2nd intensity profile |
| 103.3 | 3rd intensity profile |
| 104 | Intensity tolerance |
| 105 | Distance from the connecting zone/input coupling point |
| 106.1 | 1st intensity profile |
| 106.2 | 2nd intensity profile |
| 107.1 | Specific scattering length LS1 |
| 107.2 | Specific scattering length LS2 |
| 108 | Detector |

What is claimed is:

1. An illumination system, comprising:
a laser light source;
a light guide having a proximal end and a distal end, the proximal end is connectable and/or assignable to the laser light source, wherein the light guide comprises a core surrounded by a cladding;
a diffuser element at the distal end of the light guide, the diffuser element has a radial, spherical emission characteristic, the diffuser element comprises a diffuser main body and a scattering element, the diffuser main body comprises an inorganic material, wherein the diffuser main body has a surface with a fire-polished surface quality; and
a jacket that surrounds the diffuser element, the distal end of the light guide, and an outer portion of the cladding, wherein the jacket contacts and covers the surface of the diffusor element without a gap therebetween,
wherein the jacket comprises a layer that is transparent or translucent to light emitted laterally from the diffuser element and the jacket is made from at least one material selected from the group consisting of: a liquid silicone, a thermoplastic polymer, a hot melt adhesive, a 2-component adhesive, a sol-gel glass, and a shrink tubing,
wherein the diffuser main body connected to the light guide only at an input coupling face of the light guide, and
wherein the diffuser main body has a shape selected from a group consisting of spherical, elliptical, and drop-shape.

2. The illumination system of claim 1, wherein the inorganic material is selected from a group consisting of glass, glass ceramic, glass-like substance, and any composites thereof.

3. The illumination system of claim 1, comprising an intensity distribution of emission that deviates from a mean value by no more than ±30%.

4. The illumination system of claim 1, wherein the light guide comprises a single fiber with a core, a cladding, and a light guide diameter, wherein the diffuser main body has a main body diameter in a region of the input coupling face that is greater than or at least equal in size to the light guide diameter in the region of the input coupling face.

5. The illumination system of claim 4, further comprising a ratio of the light guide diameter to the main body diameter that is ≤1.0 to 0.5.

6. The illumination system of claim 1, wherein the light guide comprises a flexible fiber bundle or a rigid fiber rod having a light guide diameter, wherein the diffuser main body has a main body diameter in a region of the input coupling face that is greater than or equal in size to the light guide diameter in the region of the input coupling face.

7. The illumination system of claim 6, further comprising a ratio of the light guide diameter to the main body diameter that is ≤1.0 to 0.5.

8. The illumination system of claim 1, further comprising a connecting zone in which an optical element and/or an intermediate medium is arranged, wherein the connecting zone is situated between the diffuser main body and the distal end of the light guide.

9. The illumination system of claim 1, wherein the diffuser main body comprises scattering centers selected from a group consisting of pores, particles, crystallites, polycrystallites, porous pigments, optically active pigments, illuminants, phosphorescence regions, fluorescence regions, colored regions, colored particles, colored crystallites, colored pigments, colorations of glass, inhomogeneities having refractive index variations, and any combination thereof.

10. The illumination system of claim 1, wherein the diffuser main body comprises scattering centers comprising inhomogeneities of inorganic material selected from a group consisting of phase separations, demixing, particulate inclusions, seeds, crystallites, and any combinations thereof.

11. The illumination system of claim 1, wherein the diffuser main body comprises scattering centers with a concentration of the scattering centers between 10 ppm and 1000 ppm and/or with a diameter or a maximum extent in one direction of 10 nm to 5000 nm.

12. The illumination system of claim 1, wherein the diffuser main body has a homogeneous distribution of scattering centers over an entire volume.

13. The illumination system of claim 1, wherein the scattering particles comprise a compound elected from a group consisting of $SiO_2$, SiN, BaO, MgO, ZnO, $Al_2O_3$, AlN, $TiO_2$, $ZrO_2$, $Y_2O_3$, any metals thereof, BN, $B_2O_3$, Ru, Os, Rh, Ir, Ag, Au, Pd, Pt, diamond-like carbon, glass ceramic particles, and any combinations thereof.

14. The illumination system of claim 1, wherein the diffuser main body comprises a material selected from a group consisting of silicate glass, borosilicate glass, Na—Al—K silicate glass, a Na—Al—K-Ca—Zn silicate glass, Na—Al—K—As—Pb silicate glass, glass ceramic, lithium aluminosilicate glass ceramic (LAS GC), cordierite glass ceramic, magnesium aluminum silicate glass ceramic, clear transparent lithium aluminosilicate glass ceramic, and clear transparent lithium aluminosilicate glass ceramic comprising light-scattering crystallites formed by targeted application of temperature/time.

15. The illumination system of claim 1, wherein the diffuser main body comprises a borosilicate glass having a composition (in % by weight):

$B_2O_3$ 15.00-40.00,
$SiO_2$ 45.00-80.00,
$R_2O$ 0.0-20.0,
R'O 0.0-20.00,
$R''O_2$ 0.0-10.00, and
$Al_2O_3$ 0.0-10.00.

16. The illumination system of claim 1, wherein the illumination system is configured for a use selected from a group consisting of a medical therapy device, a photodynamic therapy (PDT) device, a photoimmunotherapy (PIT) device, an endovenous laser treatment (EVLT) device, a laser interstitial thermal therapy (LITT) device, dental therapy device, an ophthalmology therapy device, a dermatology therapy device, photodynamic therapy (PDT) device, a detector for spectroscopic analysis, and a detector for dosimetry.

17. A method for producing a diffuser main body, comprising:
providing a glass melt made of glass selected from a group consisting of silicate glass, Na—Al—K silicate glass, Na—Al—K-Ca—Zn silicate glass, and Na—Al—K—As—Pb silicate glass;
providing scattering centers with a diameter of 10 nm to 2000 nm to the glass melt, wherein the step of providing scattering centers comprises adding scattering particles, producing chemical scattering centers, and producing thermal scattering centers;
homogenizing the glass melt until a concentration of the scattering centers is between 10 ppm in 1000 ppm;
drawing the glass melt into a glass rod with a diameter ranging from 0.1 mm to 5 mm;
cutting the glass rod into sections; and
forming the sections by a subsequent thermal process.

18. A method for producing a diffuser main body, comprising:
providing a glass melt made of glass of borosilicate glass or alkali borosilicate glass;
producing scattering centers in the glass melt;
forming the diffuser main body from the glass melt having the scattering centers; and
coating a connecting zone of the diffuser main body with a jacket, wherein the step of producing the scattering centers comprises:
thermally treating the glass melt with a temperature/time profile for phase separation in a temperature range of 500-800° C. for a time period of 1 to 150 hours sufficient to separate the glass melt into a silicate-rich phase and a boron-rich phase, and
acid leaching and/or caustic leaching the glass melt to produce an open porosity within the glass melt with dispersive phase particles or pores of the order of 200 to 700 nm and a number density of $10^8$ to $10^{12}$ $mm^{-3}$.

19. An illumination system, comprising:
a laser light source;
a light guide having a proximal end and a distal end, the proximal end is connectable and/or assignable to the laser light source; and
a diffuser element at the distal end of the light guide, the diffuser element has a radial, spherical emission characteristic, the diffuser element comprises a diffuser main body and a scattering element, the diffuser main body consists of a glass, a glass ceramic, or a glass-like substance, wherein the diffuser main body has a surface with a fire-polished surface quality.

20. An illumination system, comprising:
a laser light source;
a light guide having a proximal end and a distal end, the proximal end is connectable and/or assignable to the laser light source, wherein the light guide comprises a core surrounded by a cladding;
a diffuser element at the distal end of the light guide, the diffuser element has a radial, spherical emission characteristic, the diffuser element comprises a diffuser main body and a scattering element,
wherein the diffuser main body comprises a borosilicate glass having a composition (in % by weight):
$B_2O_3$ 15.00-40.00,
$SiO_2$ 45.00-80.00,
$R_2O$ 0.0-20.0,
$R'O$ 0.0-20.00,
$R''O_2$ 0.0-10.00, and
$Al_2O_3$ 0.0-10.00,
wherein the diffuser main body has a surface with a fire-polished surface quality; and
a jacket that surrounds the diffuser element, the distal end of the light guide, and an outer portion of the cladding,
wherein the jacket comprises a layer that is transparent or translucent to light emitted laterally from the diffuser element and has at least one feature selected from the group consisting of: liquid silicone, thermoplastic polymer, hot melt adhesive, 2-component adhesive, sol-gel glass, and a shrink tubing,
wherein the diffuser main body connected to the light guide only at an input coupling face of the light guide, and
wherein the diffuser main body has a shape selected from a group consisting of spherical, elliptical, and drop-shape.

21. The illumination system of claim 20, further comprising an intensity distribution of emission that deviates from a mean value by no more than ±30%.

22. The illumination system of claim 20, wherein the light guide comprises a single fiber with a core, a cladding, and a light guide diameter, wherein the diffuser main body has a main body diameter in a region of the input coupling face that is greater than or at least equal in size to the light guide diameter in the region of the input coupling face.

23. The illumination system of claim 22, further comprising a ratio of the light guide diameter to the main body diameter that is ≤1.0 to 0.5.

24. The illumination system of claim 20, wherein the light guide comprises a flexible fiber bundle or a rigid fiber rod having a light guide diameter, and wherein the diffuser main body has a main body diameter in a region of the input coupling face that is greater than or equal in size to the light guide diameter in the region of the input coupling face.

25. The illumination system of claim 24, further comprising a ratio of the light guide diameter to the main body diameter that is ≤1.0 to 0.5.

26. The illumination system of claim 20, further comprising a connecting zone in which an optical element and/or an intermediate medium is arranged, wherein the connecting zone is situated between the diffuser main body and the distal end of the light guide.

27. The illumination system of claim 20, wherein the diffuser main body comprises scattering centers selected from a group consisting of pores, particles, crystallites, polycrystallites, porous pigments, optically active pigments, illuminants, phosphorescence regions, fluorescence regions, colored regions, colored particles, colored crystallites, colored pigments, colorations of glass, inhomogeneities having refractive index variations, and any combination thereof.

28. The illumination system of claim 20, wherein the diffuser main body comprises scattering centers comprising inhomogeneities of inorganic material selected from a group consisting of phase separations, demixing, particulate inclusions, seeds, crystallites, and any combinations thereof.

29. The illumination system of claim 20, wherein the diffuser main body comprises scattering centers with a concentration of the scattering centers between 10 ppm and 1000 ppm and/or with a diameter or a maximum extent in one direction of 10 nm to 5000 nm.

30. The illumination system of claim 20, wherein the diffuser main body has a homogeneous distribution of scattering centers over an entire volume.

31. The illumination system of claim 20, wherein the scattering particles comprise a compound elected from a group consisting of $SiO_2$, SiN, BaO, MgO, ZnO, $Al_2O_3$, AlN, $TiO_2$, $ZrO_2$, $Y_2O_3$, any metals thereof, BN, $B_2O_3$, Ru, Os, Rh, Ir, Ag, Au, Pd, Pt, diamond-like carbon, glass ceramic particles, and any combinations thereof.

32. The illumination system of claim 20, wherein the illumination system is configured for a use selected from a group consisting of a medical therapy device, a photodynamic therapy (PDT) device, a photoimmunotherapy (PIT) device, an endovenous laser treatment (EVLT) device, a laser interstitial thermal therapy (LITT) device, dental therapy device, an ophthalmology therapy device, a dermatology therapy device, photodynamic therapy (PDT) device, a detector for spectroscopic analysis, and a detector for dosimetry.

* * * * *